United States Patent
Leadlay et al.

(10) Patent No.: US 6,437,151 B2
(45) Date of Patent: Aug. 20, 2002

(54) ERYTHROMYCINS AND PROCESS FOR THEIR PREPARATION

(75) Inventors: Peter Francis Leadlay; James Staunton; Jesus Cortes, all of Cambridge; Michael Stephen Pacey, Broadstairs, all of (GB)

(73) Assignees: Biotica Technology Limited, Cambridge (GB); Pfizer Inc., New York, NY (US)

( * ) Notice: Subject to any disclaimer, the term of this patent is extended or adjusted under 35 U.S.C. 154(b) by 0 days.

(21) Appl. No.: 09/896,357

(22) Filed: Jun. 29, 2001

Related U.S. Application Data

(62) Division of application No. 09/214,454, filed as application No. PCT/GB97/01810 on Jul. 4, 1997, now Pat. No. 6,271,255.
(60) Provisional application No. 60/024,188, filed on Aug. 19, 1996.

(30) Foreign Application Priority Data

Jul. 5, 1996 (GB) .............................................. 9614189
May 28, 1997 (GB) .............................................. 9710962

(51) Int. Cl.$^7$ ........................ C07D 315/00; C07H 17/08
(52) U.S. Cl. ........................ 549/271; 536/7.2; 549/13; 549/29; 549/266
(58) Field of Search ........................... 536/7.2; 549/271, 549/266, 29, 13

(56) References Cited

PUBLICATIONS

Donadio, S. et al.: An erythromycin analog produced by reprogramming of polyketide synthesis. Proc. Natl. Acad. Sci. vol. 90. pp. 7119–7123, 1993.*

* cited by examiner

*Primary Examiner*—Charanjit S. Aulakh
(74) *Attorney, Agent, or Firm*—Dann Dorfman Herrell and Skillman, P.C.

(57) ABSTRACT

Erythromycins, particularly ones with novel C-13 substituents R1 (e.g. $C_3$–$C_6$ cycloalkyl or cycloalkenyl groups) are prepared by fermenting suitable organisms in the presence of $R_1CO_2H$. A preferred organism is *Saccharopolyspora erythraea* preferably containing an integrated plasmid capable of directing synthesis of desired compounds.

10 Claims, 16 Drawing Sheets

Erythromycin A

Avermectin A1b

Rapamycin

Construction of pND30

ERYTHROMYCINS AND PROCESS FOR THEIR PREPARATION

CROSS-REFERENCE TO RELATED APPLICATIONS

This application is a Divisional application of U.S. patent application Ser. No. 09/214,454, filed Jan. 5, 1999 now U.S. Pat. No. 6,271,255, which is the U.S. National Stage Application of International Application No. PCT/GB97/01810 filed Jul. 4, 1997 and claims the benefit of U.S. Provisional Patent Application No. 60/024,188, filed Aug. 19, 1996.

BACKGROUND OF THE INVENTION

The present invention relates to novel polyketides and methods and means for preparing them, and specifically to novel erythromycins that are useful as antibacterial and antiprotozoal agents and other applications (e.g., anticancer, atherosclerosis, gastric motility reduction, etc.) in mammals, including man, as well as in fish and birds. This invention also relates to pharmaceutical compositions containing the novel compounds and to methods of treating bacterial and protozoal infections in mammals, fish, and birds by administering the novel compounds to mammals, fish and birds requiring such treatment.

Polyketide biosynthetic genes or portions of them, which may be derived from different polyketide biosynthetic gene clusters are manipulated to allow the production of novel erythromycins.

Polyketides are a large and structurally diverse class of natural products that includes many compounds possessing antibiotic or other pharmacological properties, such as erythromycin, tetracyclines, rapamycin, avermectin, polyether ionophores, and FK506. In particular, polyketides are abundantly produced by Streptomyces and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the $\beta$-keto group observed after each condensation. Examples of processing steps include reduction to $\beta$-hydroxyacyl-, reduction followed by dehydration to 2-enoyl-, and complete reduction to the saturated acylthioester. The stereochemical outcome of these processing steps is also specified for each cycle of chain extension. The biosynthesis of polyketides is initiated by a group of chain-forming enzymes known as polyketide synthases. Two classes of polyketide synthase (PKS) have been described in actinomycetes. However, the novel polyketides and processes which are the subject of this invention are synthesised by Type I PKS's, represented by the PKS's for the macrolides erythromycin, avermectin and rapamycin (FIG. 1), and consist of a different set or "module" of enzymes for each cycle of polyketide chain extension (FIG. 2A) (Cortes, J. et al. Nature (1990) 348:176–178; Donadio, S. et al. Science (1991) 252:675–679; MacNeil, D. J. et al. Gene (1992), 115:119–125; Schwecke, T. et al. Proc. Natl. Acad. Sci. USA (1995) 92:7839–7843). Note: The term "natural module" as used herein refers to the set of contiguous domains, from a $\beta$-ketoacylsynthase ("KS") gene to the next acyl carrier protein ("ACP") gene, which accomplishes one cycle of polyketide chain extension. The term "combinatorial module" is used to refer to any group of contiguous domains (and domain parts), extending from a first point in a first natural module, to a second equivalent point in a second natural module. The first and second points will generally be in core domains which are present in all modules, i.e., both at equivalent points of respective KS, AT (acyl transferase), ACP domains, or in linker regions between domains.

FIG. 2 shows the organisation of the erythromycin producing PKS, (also known as 6-deoxyerythronolide B synthase, DEBS) genes. Three open reading frames encode the DEBS polypeptides. The genes are organised in six repeated units designated modules. The first open reading frame encodes the first multi-enzyme or cassette (DEBS1) which consists of three modules: the loading module (eryload) and two extension modules (modules 1 and 2). The loading module comprises an acyl transferase and an acyl carrier protein. This may be contrasted with FIG. 1 of WO 93/13663 (referred to below). This shows ORF1 to consist of only two modules, the first of which is in fact both the loading module and the first extension module.

In-frame deletion of the DNA encoding part of the ketoreductase domain of module 5 in DEBS has been shown to lead to the formation of erythromycin analogues 5,6-dideoxy-3-mycarosyl-5-oxoerythronolide B, 5,6-dideoxy-5-oxoerythronolide B and 5,6-dideoxy-6,6-epoxy-5-oxoerythronolide B (Donadio, S. et al. Science, (1991) 252:675–679) Likewise, alteration of active site residues in the enoylreductase domain of module 4 in DEBS, by genetic engineering of the corresponding PKS-encoding DNA and its introduction into Saccharopolyspora erythraea, led to the production of 6,7-anhydroerythromycin C (Donadio S. et al. Proc. Natl. Acad. Sci. USA (1993) 90:7119–7123).

International Patent Application number WO 93/13663, which is incorporated herein by reference in its entirety, describes additional types of genetic manipulation of the DEBS genes that are capable of producing altered polyketides. However, many such attempts are reported to have been unproductive (Hutchinson C. R. and Fujii, 1. Annu. Rev. Microbiol. (1995) 49:201–238, at p.231). The complete DNA sequence of the genes from Streptomyces hygroscopicus that encode the modular Type 1 PKS governing the biosynthesis of the macrocyclic immunosuppressant polyketide rapamycin has been disclosed (Schwecke, T. et al. (1995) Proc. Natl. Acad. Sci. USA 92:7839–7843) (FIG. 3). The DNA sequence is deposited in the EMBL Genbank Database under the accession number X86780.

Although large numbers of therapeutically important polyketides have been identified, there remains a need to obtain novel polyketides that have enhanced properties or possess completely novel bioactivity. The complex polyketides produced by modular Type I PKS's are particularly valuable, in that they include compounds with known utility as anthelminthics, insecticides, immunosuppressants, antifungal, and/or antibacterial agents. Because of their structural complexity, such novel polyketides are not readily obtainable by total chemical synthesis, or by chemical modifications of known polyketides. One aspect of the invention arises from our appreciation that a Type I PKS gene assembly encodes a loading module which is followed by extension modules. It is particularly useful to provide a hybrid PKS gene assembly in which the loading module is heterologous to the extension modules and is such as to lead to a polyketide having an altered starter unit. This is a concept quite unknown to the prior art since this does not recognise the existence of loading modules. WO93/13663 refers to altering PKS genes by inactivating a single function (i.e. a single enzyme) or affecting "an entire module" by deletion, insertion, or replacement thereof. The loading assembly, in their terms, is not a module.

If the loading module is one which accepts many different carboxylic acid units, then the hybrid gene assembly can be used to produce many different polyketides. For example, a hybrid gene assembly may employ nucleic acid encoding an avr loading module with ery extender modules. A loading module may accept unnatural acid units and derivatives thereof; the avr loading module is particularly useful in this regard (Dutton et al., (1991) J. Antibiot., 44:357–365). In addition, it is possible to determine the specificity of the natural loading module for unnatural starter units and to take advantage of the relaxed specificity of the loading module to generate novel polyketides. Thus, another aspect of this invention is the unexpected ability of the ery loading module to incorporate unnatural carboxylic acids and derivatives thereof to produce novel erythromycins in erythromycin-producing strains containing only DEBS genes. Of course one may also make alterations within a product polyketide particularly by replacing an extension module by one that gives a ketide unit at a different oxidation state and/or with a different stereochemistry. It has generally been assumed that the stereochemistry of the methyl groups in the polyketide chain is determined by the acyltransferase, but it is, in fact, a feature of other domains of the PKS and thus open to variation only by replacement of those domains, individually or by module replacement. Methyl and other substituents can be added or removed by acyltransferase domain replacement or total module replacement. Consequently, it also becomes apparent to those skilled in the art that it is possible to combine the use of the relaxed substrate specificity of the erythromycin loading module with extension module replacement and hybrid loading module substitution with extension module replacement as a mechanism to produce a wide range of novel erythromycins. Thus, this invention describes the production of novel erythromycins by non-transformed organisms and also such gene assemblies, vectors containing such gene assemblies, and transformant organisms that can express them to produce novel erythromycins in transformed organisms. Transformant organisms may harbour recombinant plasmids, or the plasmis may integrate. A plasmid with an int sequence will integrate into a specific attachment site (att) of a host's chromosome. Transformant organisms may be capable of modifying the initial products, e.g., by carrying out all or some of the biosynthetic modifications normal in the production of erythromycins (as shown in FIG. 2B). However, use may be made of mutant organisms such that some of the normal pathways are blocked, e.g., to produce products without one or more "natural" hydroxy-groups or sugar groups, for instance as described in WO 91/16334 or in Weber et al. (1985) J. Bacteriol. 164:425–433 which are incorporated herein by reference in their entirety. Alternatively, use may be made of organisms in which some of the normal pathways are overexpressed to overcome potential rate-limiting steps in the production of the desired product, for instance as described in WO 97/06266 which is incorporated herein by reference in its entirety.

This aspect of the method is largely concerned with treating PKS gene modules as building blocks that can be used to construct enzyme systems, and thus novel erythromycin products, of desired types. This generally involves the cutting out and the assembly of modules and multi-module groupings. Logical places for making and breaking inter-modular connections are be in the linking regions between modules. However, it may be preferable to make cuts and joins actually within domains (i.e., the enzyme-coding portions), close to the edges thereof. The DNA is highly conserved here between all modular PKS's, and this may aid in the construction of hybrids that can be transcribed. It may also assist in maintaining the spacing of the active sites of the encoded enzymes, which may be important. For example, in producing a hybrid gene by replacing the ery loading module by an avr loading module, the ery module together with a small amount of the following ketosynthase (KS) domain was removed. The start of the KS domain (well spaced from the active site) is highly conserved and therefore provides a suitable splicing site as an alternative to the linker region between the loading domain and the start of the KS domain. The excised ery module was then replaced by an avr loading module.

In fact, when substituting a loading module, it may be desirable to replace not just the loading module domains (generally acyl transferase (AT) and acyl carrier protein (ACP)), but also the KS at the start of the following extension module. Typically. the excised loading module would have provided a propionate starter, and the replacement is intended to provide one or more different starters. Propionate, however, may feed into the KS of the extension module from a propionate pool in the host cell, leading to dilution of the desired products. This can be largely prevented by substituting an extended loading module including all or most of the KS domain. (The splice site may be in the end region of the KS gene, or early in the following AT gene, or the linker region between them.)

When replacing "modules", one is not restricted to "natural" modules. For example, a "combinatorial module" to be excised and/or replaced and/or inserted may extend from the corresponding domain of two natural-type modules, e.g., from the AT of one module to the AT of the next, or from KS to KS. The splice sites will be in corresponding conserved marginal regions or in linker regions. A combinatorial module can also be a 'double' or larger multiple, for adding 2 or more modules at a time.

In a further aspect, the invention provides novel erythromycins obtainable by means of the previous aspects. These include the following:

(i) An erythromycin analogue (being a macrolide compound with a 14-membered ring) in which C-13 bears a side-chain other than ethyl, generally a straight chain C3–C6 alkyl group, a branched $C_3$–$C_8$ alkyl group, a $C_3$–$C_8$ cycloalkyl or cycloalkenyl group (optionally substituted, e.g., with one or more hydroxy, $C_1$-alkyl or alkoxy groups or halogen atoms), or a 3–6 membered heterocycle containing O or S, saturated or fully or partially unsaturated, optionally substituted (as for cycloalkyl), or $R_1$ is phenyl which may be optionally substituted with at least one substituent selected from $C_1$–$C_4$ alkyl, $C_1$–$C_4$ alkoxy and $C_1$–$C_4$ alkylthio groups, halogen atoms, trifluoromethyl, and cyano; or $R_1$ may be a group with a formula (a) as shown below:

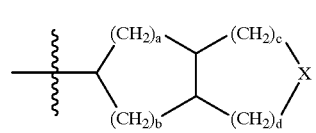

wherein X is O, S or —$CH_2$—, a, b, c, and d are each independently 0–2 and a+b+c+d≦5. Preferred candidates for the C-13 substituent R are the groups of carboxylate units RCOOR', usable as substrates by an avr starter module, or rapamycin starter variants Preferred substrates are the carboxylic acids RCOOH. Alternative substrates that can be effectively used are carboxylic acid salts, carboxylic acid esters, or amides. Preferred esters are N-acetyl-cysteamine thioesters which can readily be utilised as substrates by the avr starter module as illustrated by Dutton et al. in EP 0350187 which is incorporated herein by reference in its entirety. Preferred amides are N-acyl imidazoles. Other alternative substrates that may be used are derivatives which are oxidative precursors for the carboxylic acids; thus, for example suitable substrates would be amino acids of the formula $RCH(NH_2)COOH$, glyoxylic acids of the formula RCOCOOH, methylamine derivatives of the formula $RCH_2NH_2$, methanol derivatives of the formula $RCH_2OH$, aldehydes of the formula RCHO or substituted alkanoic acids of the formula $R(CH_2)_nCOOH$ wherein n is 2, 4, or 6. Thus examples of preferred substrates include isobutyrate (R=i-Pr) and 2-methylbutyrate (R=1-methylpropyl). Other possibilities include n-butyrate, cyclopropyl carboxylate, cyclobutyl carboxylate, cyclopentyl carboxylate cyclohexyl carboxylate, cycloheptanyl carboxylate, cyclohexenyl carboxylates, cycloheptenyl carboxylates, and ring-methylated variants of the cyclic carboxylates and the aforementioned derivatives thereof.

The erythromycin analogue may correspond to the initial product of a PKS (6-deoxyerythronolide) or the product after one or more of the normal biosynthetic steps. As shown in FIG. 2b these comprise: 6-hydroxylation; 3–0-glycosylation; 5–0-glycosylation; 12-hydroxylation; and specific sugar methylation.

Thus, the analogues may include those corresponding to 6-deoxyerythronolide B, erythromycin A, and the various intermediates and alternatives (although not limited to those) shown in FIG. 2b.

(ii) Erythromycin analogues differing from the corresponding 'natural' compound (FIG. 2b) in the oxidation state of one or more of the ketide units (i.e. selection of alternatives from the group: —CO—, —CH(OH)—, =CH—, and —CH$_2$—).

The stereochemistry of any —CH(OH)— is also independently selectable.

(iii) Erythromycin analogues differing from the corresponding 'natural' compound in the absence of a 'natural' methyl side-chain. (This is achievable by use of a variant AT). Normal extension modules use either $C_2$ or $C_3$ units to provide unmethylated and methylated ketide units. One may provide unmethylated units where methylated units are natural (and vice versa, in systems where there are naturally unmethylated units) and also provide larger units, e.g., $C_4$ to provide ethyl substituents.

(iv) Erythromycin analogues differing from the corresponding 'natural' compound in the stereochemistry of 'natural' methyl; and/or ring substituents other than methyl.

(v) Erythromycin analogues having the features of two or more of sections (i) to (iv).

(vi) Derivatives of any of the above which have undergone further processing by non-PKS enzymes, e.g., one or more of hydroxylation, epoxidation, glycosylation, and methylation.

Methods are described for the production of the novel erythromycins of the present invention. In the simplest method, unnatural starter units (preferably, but not restricted to the carboxylic acid analogues of the unnatural starter units) are introduced to untransformed organisms capable of producing erythromycins. A preferred approach involves introduction of the starter unit into fermentation broths of the erythromycin-producing organism, an approach which is more effective for transformed organisms capable of producing erythromycins. However, the starter unit analogue can also be introduced to alternative preparations of the erythromycin-producing organisms, for example, fractionated or unfractionated broken-cell preparations. Again, this approach is equally effective for transformed organisms capable of producing erythromycins. In another method, one or more segments of DNA encoding individual modules or domains within a heterologous Type I PKS (the "donor" PKS) have been used to replace the DNA encoding, respectively, individual modules or domains within the DEBS genes of an erythromycin-producing organism. Loading modules and extension modules drawn from any natural or non-natural Type I PKS, are suitable for this "donor" PKS but particularly suitable for this purpose are the components of Type I PKS's for the biosynthesis of erythromycin, rapamycin, avermectin, tetronasin, oleandomycin, monensin, amphotericin, and rifamycin, for which the gene and modular organisation is known through gene sequence analysis, at least in part. Particularly favourable examples of the loading modules of the donor PKS are those loading modules showing a relaxed specificity, for example, the loading module of the avermectin (avr)-producing PKS of *Streptomyces avermitilis*; or those loading modules possessing an unusual specificity, for example, the loading modules of the rapamycin-, FK506- and ascomycin-producing PKS's, all of which naturally accept a shikimate-derived starter unit. Unexpectedly, both the untransformed and genetically engineered erythromycin-producing organisms when cultured under suitable conditions have been found to produce non-natural erythromycins, and where appropriate, the products are found to undergo the same processing as the natural erythromycin.

In a further aspect of the present invention, a plasmid containing "donor" PKS DNA is introduced into a host cell under conditions where the plasmid becomes integrated into the DEBS genes on the chromosome of the erythromycin-producing strain by homologous recombination, to create a hybrid PKS. A preferred embodiment is when the donor PKS DNA includes a segment encoding a loading module in such a way that this loading module becomes linked to the DEBS genes on the chromosome. Such a hybrid PKS produces valuable and novel erythromycin products when cultured under suitable conditions as described herein. Specifically, when the loading module of the DEBS genes is replaced by the loading module of the avermectin-producing (avr) PKS, the novel erythromycin products contain a starter unit typical of those used by the avr PKS. Thus, when the loading module of the ery PKS is replaced by the avr loading module, *Saccharopolyspora erythraea* strains containing such hybrid PKS are found to produce 14-membered macrolides containing starter units typically used by the avr PKS.

It is unexpected that the 14-membered macrolide polyketides produced by such recombinant cells of *S. erythraea* are found to include derivatives of erythromycin A, showing that the several processing steps required for the transformation of the products of the hybrid PKS into novel and therapeutically valuable erythromycin A derivatives are correctly carried out. A further aspect of the present invention is the unexpected and surprising finding that transcription of any of the hybrid erythromycin genes can be specifically increased when the hybrid genes are placed under the control of a promoter for a Type II PKS gene linked to a specific activator gene for that promoter. It is particularly remarkable that when a genetically engineered cell containing hybrid erythromycin genes under such control is cultured under conditions suitable for erythromycin production, significantly enhanced levels of the novel erythromycin are produced. Such specific increases in yield of a valuable erythromycin product are also seen for natural erythromycin PKS placed under the control of a Type II PKS promoter and activator gene. In a preferred embodiment, desired genes present on an SCP2*-derived plasmid are placed under the control of the bidirectional actI promoter derived from the actinorhodin biosynthetic gene cluster of *Streptomyces coelicolor*, and in which the vector also contains the structural gene encoding the specific activator protein Act II-orf 4. The recombinant plasmid is introduced into *Saccharopolyspora erythraea*, under conditions where either the introduced PKS genes, or PKS genes already present in the host strain, are expressed under the control of the actI promoter.

Such strains produce the desired erythromycin product and the activator gene requires only the presence of the specific promoter in order to enhance transcriptional efficiency from the promoter. This is particularly surprising in that activators of the ActII-orf4 family do not belong to a recognised class of DNA-binding proteins. Therefore it would be expected that additional proteins or other control elements would be required for activation to occur in a heterologous host not known to produce actinorhodin or a related isochromanequinone pigment. It is also surprising and useful that the recombinant strains can produce more than ten-fold erythromycin product than when the same PKS genes are under the control of the natural promoter, and the specific erythromycin product is also produced precociously in growing culture, rather than only during the transition from growth to stationary phase. Such erythromycins are useful as antibiotics and for many other purposes in human and veterinary medicine. Thus, when the genetically engineered cell is *Saccharopolyspora erythraea*, the activator and promoter are derived from the actinorhodin PKS gene cluster and the actI/actII-orf4-regulated ery PKS gene cluster is housed in the chromosome, following the site-specific integration of a low copy number plasmid vector, culturing of these cells under suitable conditions can produce more than ten-fold total 14-membered macrolide product than in a comparable strain not under such heterologous control When in such a genetically engineered cell of *S. erythraea* the PKS genes under this heterologous control are hybrid Type I PKS genes whose construction is described herein, more than ten-fold hybrid polyketide product can be obtained compared to the same hybrid Type I PKS genes not under such control. Specifically, when the hybrid Type I PKS genes are the ery PKS genes in which the loader module is replaced by the avr loading module, a ten-fold increase is found in the total amounts of novel 14-membered macrolides produced by the genetically engineered cells when cultured under suitable conditions as described herein.

The suitable and preferred means of growing the untransformed and genetically-engineered erythromycin-producing cells, and suitable and preferred means for the isolation, identification, and practical utility of the novel erythromycins are described more fully in the examples.

SUMMARY OF THE INVENTION

The present invention relates to compounds of the formula 1:

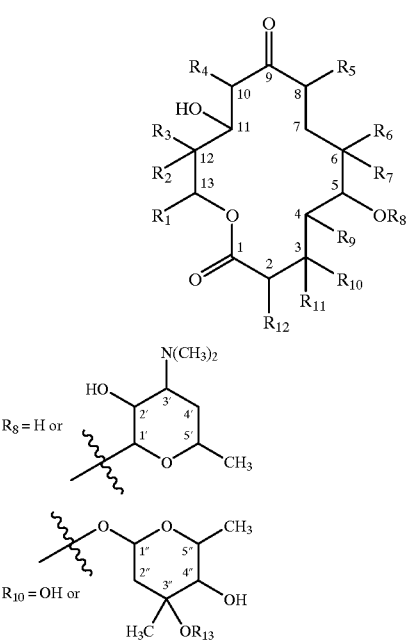

and to pharmaceutically acceptable salts thereof, wherein:

$R_1$ is an alpha-branched $C_3$–$C_8$ alkyl, alkenyl, alkynyl, alkoxyalkyl or alkylthioalkyl group any of which may be optionally substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R_1$ is phenyl which may be optionally substituted with at least one substituent selected from $C_1$–$C_4$ alkyl, $C_1$–$C_4$ alkoxy and $C_1$–$C_4$ alkylthio groups, halogen atoms, trifluoromethyl, and cyano; or $R_1$ may be a group with a formula (a) as shown below:

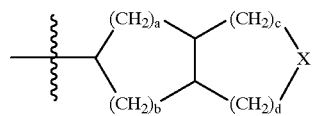

wherein X is O, S or —CH$_2$—, a, b, c, and d are each independently 0–2 and a+b+c+d≦5.

$R_2$ is H or OH; $R_3$–$R_5$ are each, independently H, $CH_3$, or $CH_2CH_3$; $R_6$ is H or OH; and $R_7$ is H, $CH_3$, or $CH_2CH_3$; $R_8$ is H or desosamine; $R_9$ is H, $CH_3$, or $CH_2CH_3$; $R_{10}$ is OH, mycarose ($R_{13}$ is H), or cladinose ($R_{13}$ is $CH_3$), $R_{11}$ is H; or $R_{10}$=$R_{11}$=O; and $R_{12}$ is H, $CH_3$, or $CH_2CH_3$.

In the above definition, alkyl groups containing 3 or more carbon atoms may be straight or branched chain. Halo means fluoro, chloro, bromo or iodo. Alpha-branched means that the carbon attached to the C-13 position is a secondary carbon atom linked to two further carbon atoms, the remainder of the alkyl chain may be straight or branched chain.

Preferred compounds of formula 1 are those wherein $R_3$-$R_5$, $R_7$, $R_9$, and $R_{12}$ are $CH_3$, and $R_1$ is isopropyl or sec-butyl, 2-buten-2-yl, 2-penten-2-yl, or 4-methyl-2- penten-2-yl optionally substituted by one or more hydroxyl groups. Also preferred are compounds of formula 1 wherein $R_3$-$R_5$, $R_7$, $R_9$ and $R_{12}$ are $CH_3$, and $R_1$ is $C_3$-$C_6$ cycloalkyl or cycloalkenyl, which may optionally be substituted by one or more hydroxyl groups or one or more $C_1$-$C_4$ alkyl groups. In a further group of preferred compounds, $R_1$ is a 5 or 6 membered oxygen or sulphur containing heterocyclic ring, particularly a 3-thienyl or 3-furyl ring, which may be optionally substituted by one or more hydroxyl groups, or one or more $C_1$-$C_4$ alkyl groups or halogen atoms. In another group of preferred compounds, $R_1$ is a $C_3$-$C_8$ alkylthioalkyl group, particularly a 1-methylthioethyl group Other specific embodiments of this invention include compounds of formula 2:

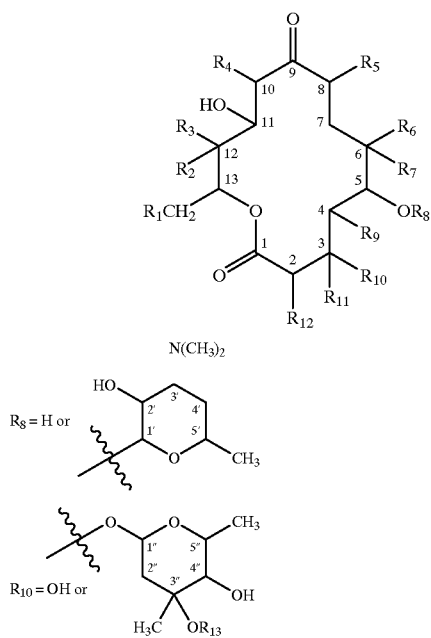

and to pharmaceutically acceptable salts thereof, wherein:

$R_1$ is H, $C_1$-$C_8$ alkyl, $C_2$-$C_8$ alkenyl, $C_2$-$C_8$ alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$-$C_8$ cycloalkyl or $C_5$-$C_8$ cycloalkenyl either of which may be optionally substituted by methyl or one or more $C_1$-$C_4$ alkyl groups or halo atoms; or a 3 to 6 membered oxygen or sulphur containing heterocyclic ring which may be saturated or fully or partially unsaturated and which may optionally be substituted by one or more $C_1$-$C_4$ alkyl groups or halo atoms; or a group of the formula $SR_{14}$ wherein $R_{14}$ is $C_1$-$C_8$ alkyl, $C_2$-$C_8$ alkenyl, $C_2$-$C_8$ alkynyl, $C_3$-$C_8$ cycloalkyl, $C_5$-$C_8$ cycloalkenyl, phenyl or substituted phenyl wherein the substituent is $C_1$-$C_4$ alkyl, $C_1$-$C_4$ alkoxy or halo, or a 3 to 6 membered oxygen or sulphur-containing heterocyclic ring which may be saturated, or fully or partially unsaturated and which may optionally be substituted by one or more $C_1$-$C_4$ alkyl groups or halo atoms.

$R_2$ is H or OH; $R_3$-$R_5$ are each independently H, $CH_3$, or $CH_2CH_3$; $R_6$ is H or OH; and $R_7$ is H, $CH_3$, or $CH_2CH_3$; $R_8$ is H or desosamine; $R_9$ is H, $CH_3$, or $CH_2CH_3$; $R_{10}$ is OH, mycarose ($R_{13}$ is H), or cladinose ($R_{13}$ is $CH_3$), $R_{11}$ is H; or $R_{10}$=$R_{11}$=O; and $R_{12}$ is H, $CH_3$, or $CH_2CH_3$, with the proviso that when $R_3$-$R_5$ are $CH_3$, $R_7$ is $CH_3$, $R_9$ is $CH_3$, and $R_{12}$ is $CH_3$, then $R_1$ is not H or $C_1$ alkyl.

In the above definition, alkyl groups containing 3 or more carbon atoms may be straight or branched chain. Halo means fluoro, chloro, bromo or iodo.

Preferred compounds of formula 2 are those wherein $R_3$-$R_5$ are $CH_3$, $R_7$ is $CH_3$, $R_9$ is $CH_3$, and $R_{12}$ is $CH_3$, and $R_1$ is $SR_{14}$ wherein $R_{14}$ is methyl or ethyl. In another group of preferred compounds, $R_1$ is methyl, isopropyl, or sec-butyl, which may be substituted by one or more hydroxyl groups. In a further group of preferred compounds, $R_1$ is branched $C_3$-$C_8$ alkyl group substituted by one or more hydroxyl groups or one or more halo atoms, particularly 1-(trifluoromethyl) ethyl.

The invention also relates to a pharmaceutical composition for the treatment of a bacterial infection or a protozoal infection in a mammal, fish, or bird which comprises a therapeutically effective amount of a compound of formula 1 or formula 2, or a pharmaceutically acceptable salt thereof, and a pharmaceutically acceptable carrier.

The invention also relates to a method of treating a bacterial infection or a protozoal infection in a mammal, fish, or bird which comprises administering to said mammal, fish or bird a therapeutically effective amount of a compound of formula 1 or formula 2 or a pharmaceutically acceptable salt thereof.

The term "treatment", as used herein, unless otherwise indicated, includes the treatment or prevention of a bacterial infection or protozoal infection as provided in the method of the present invention.

As used herein, unless otherwise indicated, the terms "bacterial infection(s)" and "protozoal infection(s)" include bacterial infections and protozoa infections that occur in mammals, fish and birds as well as disorders related to bacterial infections and protozoal infections that may be treated or prevented by administering antibiotics such as the compounds of the present invention. Such bacterial infections and protozoal infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus spp.*; pharyngitis, rheumatic fever, and glomerylonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chiamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by

*Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* gastroenteritis related to infection by *Campytobacter jejuni;* intestinal protozoa related to infection by Cryptosporidium spp.; odontogenic infection related to infection by viridans streptococci; persistent cough related to infection by *Bordetella pertussis*; gas gangrene related to infection by *Clostridium perfringens or* Bacteroides spp.; and atherosclerosis related to infection by *Helicobacter pylori* or *Chlamydia pneumoniae.* Bacterial infections and protozoal infections and disorders related to such infections that may be treated or prevented in animals include the following: bovine respiratory disease related to infection by *P. haem., P. multocida, Mycoplasma bovis,* or Bordetella spp.; cow enteric disease related to infection by *E.coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli* cow hairy warts related to infection by *Fusobacterium necrophorum* or *Bacteroides nodosus;* cow pink-eye related to infection by *Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius, coagulase* neg. Staph. or *P. muftocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996). It is also becoming increasingly apparent that compounds of this invention can have considerable utility in the treatment of disease states (e.g., cancer, AIDS, and atherosclerosis) not normally associated with bacterial or protozoal infections.

When used to treat a bacterial infection or a disorder related to a bacterial infection or cancer in a mammal, such as a human, or a fish, or bird, a compound of formula 1 or formula 2 can be administered alone or in the form of a pharmaceutical composition comprising the compound and a pharmaceutically acceptable diluent or carrier. Such compositions can be administered orally, for example, as tablets or capsules, or parenterally, which includes subcutaneous and intramuscular injection. The compounds of formula 1 or formula 2 may also be administered rectally such as through application of a suppository. The pharmaceutically acceptable carrier will depend on the intended mode of administration. For example, lactose, sodium citrate, and salts of phosphoric acid, together with disintegrating agents (such as starch) and lubricating agents (such as magnesium stearate, sodium laurel sulfate, and talc) can be used as the pharmaceutically acceptable carrier in tablets. Also, for use in capsules, useful pharmaceutically acceptable carriers are lactose and high molecular weight polyethylene glycols (e.g., having molecular weights from 2,000 to 4,000). For parenteral use, sterile solutions, or suspensions can be prepared wherein the pharmaceutically acceptable carrier is aqueous (e.g., water, isotonic saline, or isotonic dextrose) or non-aqueous (e.g., fatty oils of vegetable origin such as cottonseed or peanut oil, of polyols such as glycerol or propylene glycol).

When used in vivo to treat a bacterial infection or orders related to a bacterial infection in a mammalian subject, or for treatment of various cancers in humans, (in particular non-small cell lung cancer) and other mammals such as dogs, either orally or parenterally, the usual daily dosage will be in the range from 0.1–100 mg/kg of body weight, especially 0.5–25 mg/kg of body weight, in single or divided doses.

The phrase "pharmaceuticaly acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronte, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon other atoms are replaced by isotopes thereof. Such compounds may be useful as research and diagnostic tools in metabolism pharmacokinetic studies and in binding assays.

Compounds of the present invention are produced by fermentation of an untransformed or transformed organism capable of producing erythromycins, including but not limited to Saccharopolyspora species, *Streptomyces griseoplanus,* Nocardia sp., Micromonospora sp., Arthobacter sp., and *Streptomyces antibioticus,* but excluding *S. coelicolor.* Particularly suitable in this regard are untransformed and transformed strains of *Saccharopolyspora erythraea,* for example NRRL 2338, 18643, 21484. Particularly preferred transformed strains are those in which the erythromycin loading module has been replaced with the loading module from the avermectin producer, *Streptomyces avermitilis,* or the rapamycin producer, *Streptomyces hygroscopicus.* The preferred method of producing compounds of the current invention is by fermentation of the appropriate organism in the presence of the appropriate carboxylic acid of the formula R1COOH, wherein R1 is as previously defined in formulas 1 or 2, or a salt, ester(particularly preferable being the N-acetylcysteamine thioester), or amide thereof or oxidative precursor thereof. The acid or derivative thereof is added to the fermentation either at the time of inoculation or at intervals during the fermentation. Production of the compounds of this invention may be monitored by removing samples from the fermentation, extracting with an organic solvent and following the appearance of the compounds of this invention by chromatography, for example using high pressure liquid chromatography. Incubation is continued until the yield of the compound of formulae 1 or 2 has been maximised, generally for a period of 4 to 10 days. A preferred level of each addition of the carboxylic acid or derivative there of is between 0.05 and 4.0 g/L. The best yields of the compounds from formulae 1 or 2 are generally by gradual adding the acid or derivative to the fermentation, for example by daily addition over a period of several days. The medium used for the fermentation may be a convention a complex medium containing assimilable sources of carbon, nitrogen and trace elements.

The suitable and preferred means of growing the untransformed and genetically-engineered erythromycin-producing cells, and suitable and preferred means for the isolation, identification, and practical utility of the compounds of formulae 1 and 2 are described more fully in the Examples.

BRIEF DESCRIPTION OF THE DRAWINGS

Some embodiments of the invention will now be described with reference to the accompanying drawings in which.

DETAILED DESCRIPTION OF THE INVENTION

Figure 1:
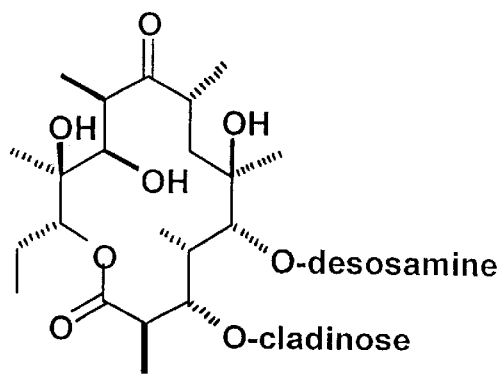
FIG. 1 gives the chemical formulae of three known polyketides.
Figure 1:
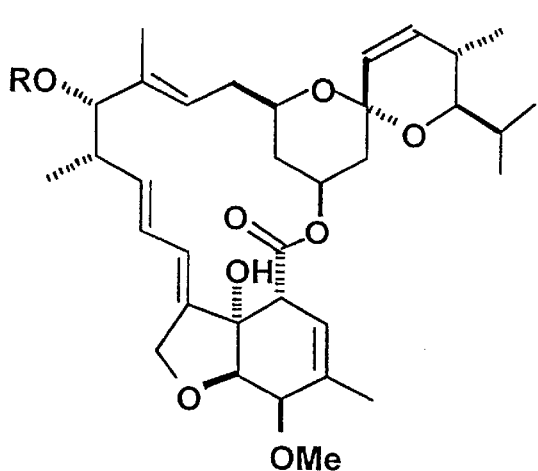
Figure 1:
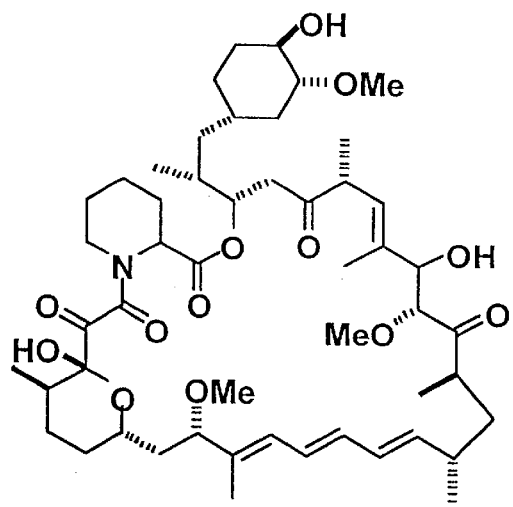
Figure 2A:
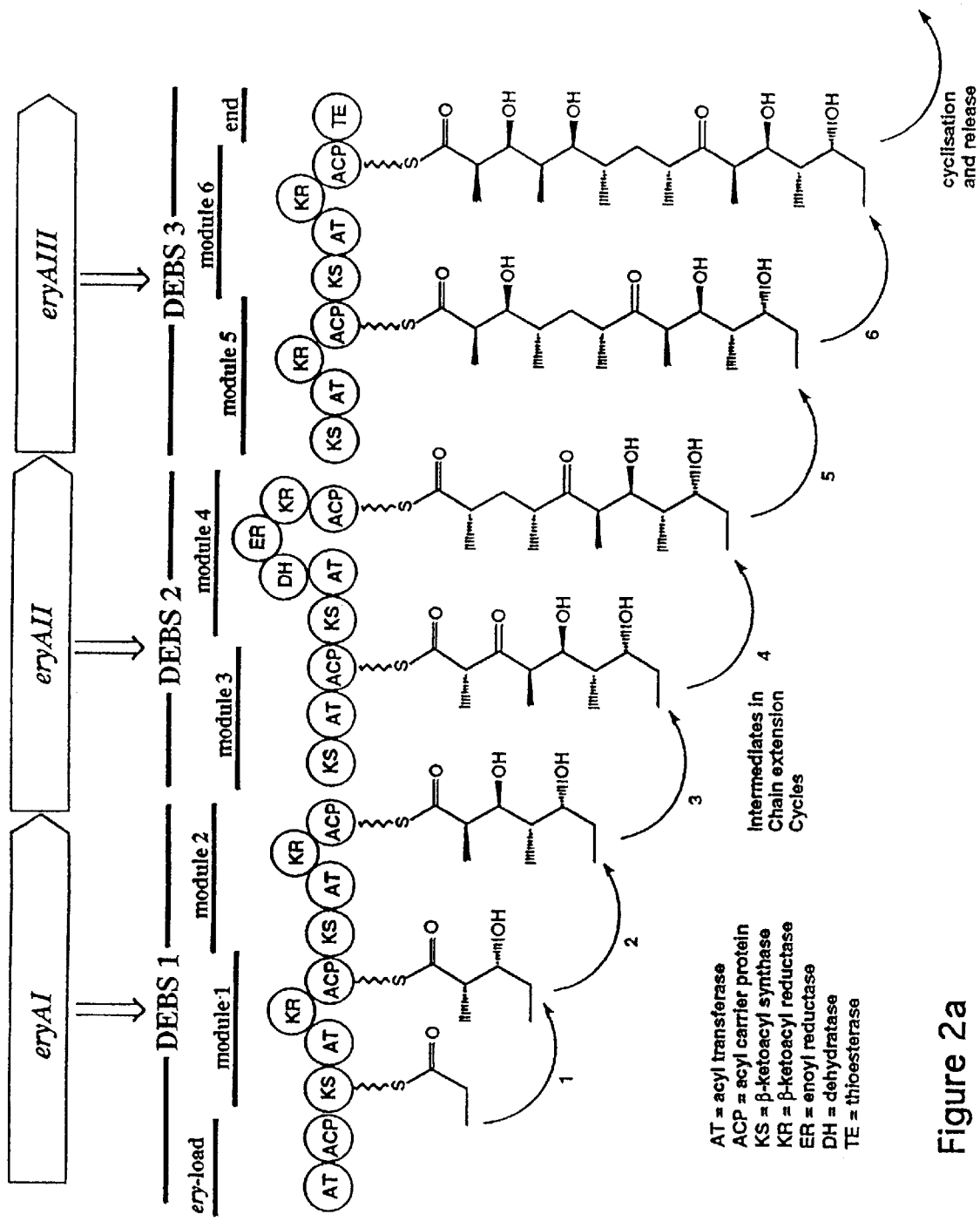
FIG. 2a is a diagram showing the functioning of 6-deoxyerythronolide synthase B (DEBS), a PKS producing 6-deoxyerythronolide B (6-DEB), a precursor of erythromycin A.
Figure 2B:
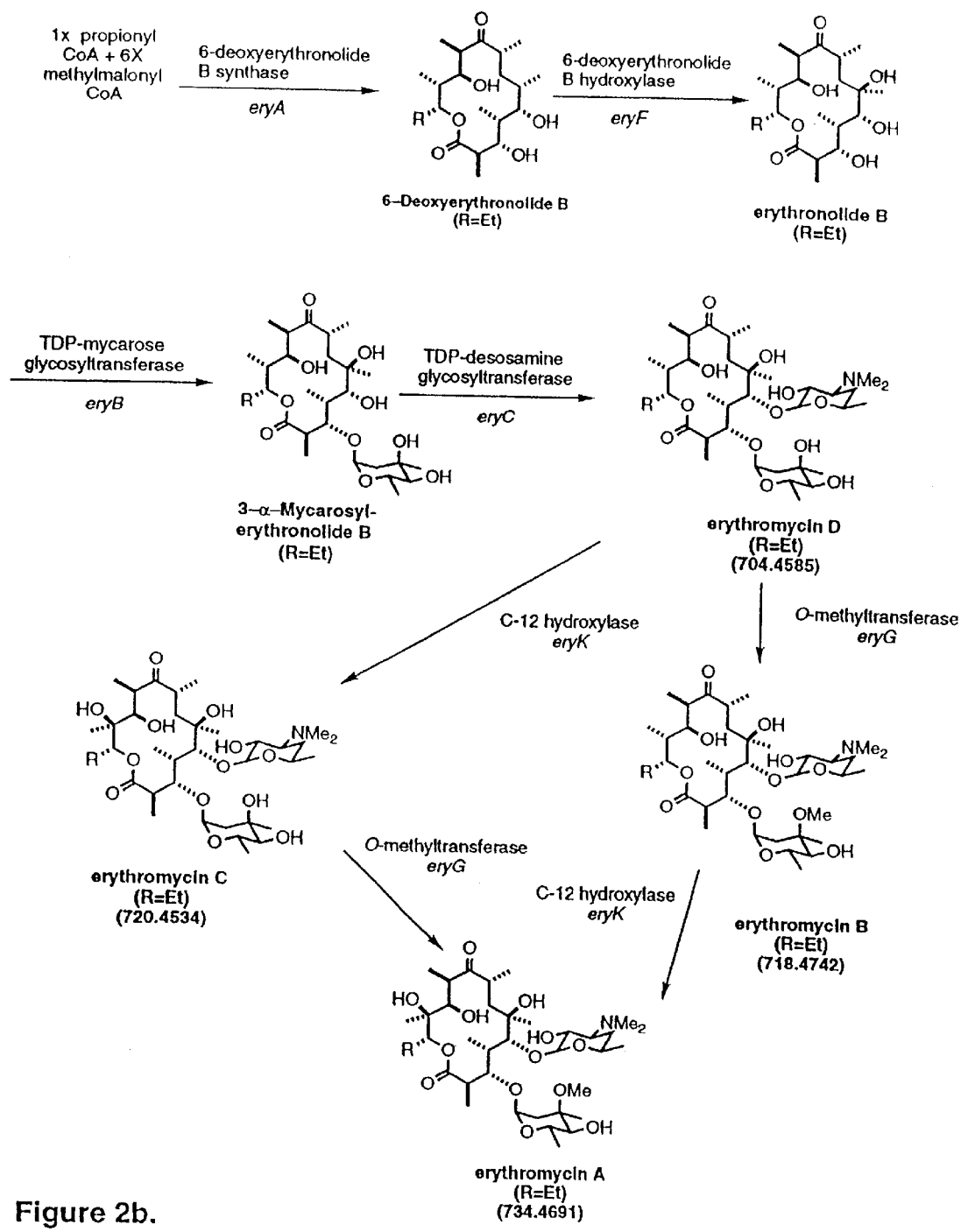
FIG. 2b shows post-PKS biosynthesis of erythromycins including the conversion of 6-DEB to erythromycin A.

The wide range of starter units accepted by the avr loading module has been comprehensively established in previous studies (for example European Patent Applications 0 214 731, 0 350 187, 0 317 148 which are incorporated herein in their entirety). Consequently, it should be understood that the invention is not limited to the specific detail of these examples and they simply serve to confirm the effectiveness of the avr loading module. Furthermore, the examples using the pIG1 or pND30 construct clearly demonstrate the capability of the actI promoter and its cognate activator gene actII-orf4 to enhance the expression of the novel compounds of this invention when linked to the avr loading module. It is also apparent from the examples that untransformed strains of Saccharopolyspora erythraea are also readily capable of taking up exogenously-supplied substrates to generate novel erythromycin polyketides. Consequently, it is also apparent to those skilled in the art that specific novel compounds of this invention can be readily produced by selection of the appropriate erythromycin producing strain (optionally incorporating the pIG1 or pND30 plasmid into the desired strain), and supplementing the fermentation with the appropriate starter unit. Thus, 6-deoxyerythromycin and 6,12-dideoxyerythromycin derivatives of the present invention can be readily produced using Saccharopolyspora erythraea NRRL 18643 or NRRL 21484 as indicated in U.S. Pat. No. 5,141,926 and WO 97/06266. Similarly, use of the Saccharopolyspora erythraea strains described by Weber et al. in J. Bacteriol., 164:425–433, 1991 can also be employed to obtain the desired novel analogues of the present invention. For example, strain UW24 can be used (optionally transformed by pIG1 or pND30) to obtain novel analogues of erythronolide B.

UV spectra were recorded using a Hewlett-Packard 1090M diode-array spectrophotometer. All NMR spectra were measured in $CDCl_3$ by a Varian Unity 500 MHz spectrometer unless otherwise indicated and peak positions are expressed in parts per million (ppm) downfield from tetramethysilane. The peak shapes are denoted as follows: s, singlet; d, doublet; t, triplet; q, quartet; m, multiplet; br, broad. The atom number shown in the NMR structures is not representative of standard nomenclature, but correlates NMR data to that particular example. HPLC-MS data was acquired using a Hewlett-Packard 1090M liquid chromatograph interfaced to a VG Platform II mass spectrometer equipped with an APCI source (method A) or using a Hewlett-Packard 1050 liquid chromatograph interfaced to a VG Platform II mass spectrometer equipped with an APCI source (method B and method C).

HPLC method A:
  Column Beckman Ultrasphere 5 µm ODS 4 mm×25 cm
  Flow 0.85 mL/min
  Mobile phase Gradient: acetonitrile:0.05 M ammonium acetate (28:72) to acetonitrile:0.05 M ammonium acetate (50:50) over 22 minutes, maintain acetonitrile:0.05 M ammonium acetate (50:50) 22–25 minutes; return to initial conditions 25–30 minutes.

HPLC method B:
  Column MetaChem Inertsil 5 µm C8 3 mm×150 mm
  Flow 0.5 mL/min
  Mobile phase Isocratic: methanol:0.05 M ammonium acetate with 0.1% trifluoroacetic acid (60:40)

HPLC method C.
  Column Waters Symmetry 5 µm C18 2.1 mm×150 mm
  Flow 0.22 mL/min
  Mobile phase Gradient: acetonitrile:0.05 M ammonium acetate (30:70) to acetonitrile:0.05 M ammonium acetate (50:50) over 30 minutes.

Use is made of the following media and solutions:

Sucrose-Succinate Defined Medium

| sucrose | 69 g |
|---|---|
| $KNO_3$ | 10 g |
| succinic acid | 2.36 g |
| $KH_2PO_4$ | 2.7 g |
| $MgSO_{4.7H_2O}$ | 1.2 g |
| $ZnCl_2$ | 10 mg |
| $MnCl_{2.4H_2O}$ | 6.2 g |
| $CuCl_{2.2H_2O}$ | 0.53 mg |
| $CoCl_2$ | 0.55 mg |
| $FeSO_{4.7H_2O}$ | 2.5 mg |
| $CaCl_{2.2H_2O}$ | 38 mg |
| milli-Q water | to 1.0 L |
| KOH | to pH 6–6.4 |

Tap Water Medium

| glucose | 5 g |
|---|---|
| tryptone | 5 g |
| yeast extract | 2.5 g |
| EDTA | 36 mg |
| tap water | to 1.0 L |
| KOH | to pH 7.1 |

ERY-P Medium

| dextrose | 50 g/L |
|---|---|
| Nutrisoy ™ flour | 30 g/L |
| $(NH_4)_2SO_4$ | 3 g/L |
| NaCl | 5 g/L |
| $CaCO_3$ | 6 g/L |
| pH adjusted to 7.0 | |

Nutrisoy ™ flour is purchased from British Arkady Group, Skerton Road, Manchester, UK.

Nutrisoy™ flour is purchased from British Arkady Group, Skerton Road, Manchester, UK.

The present invention is illustrated by the following examples.

EXAMPLE 1a

Construction of Plasmid pIG1

Figure 3A:
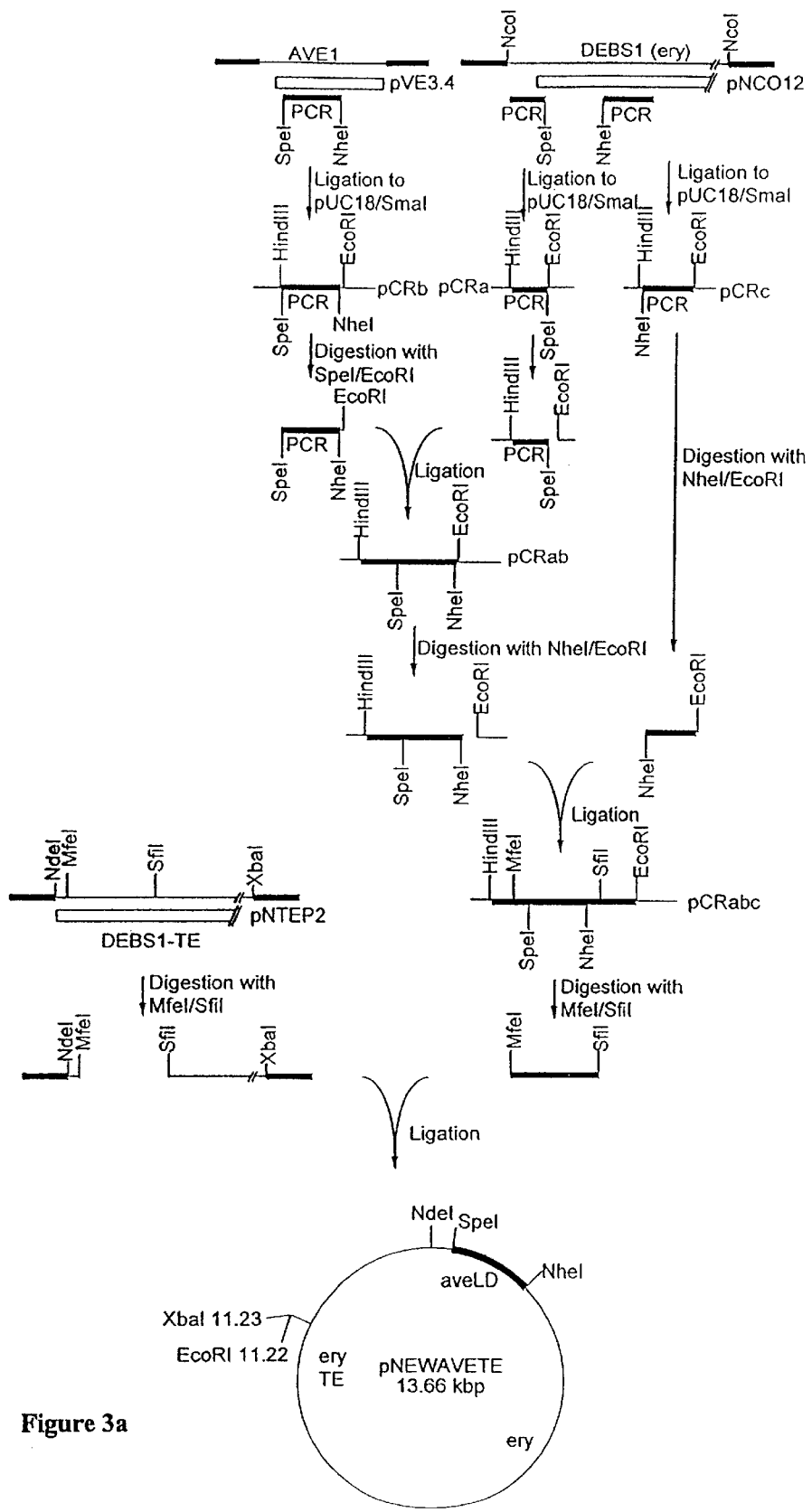
FIGS. 3a and 3b are diagrams showing the construction of plasmid pIG1.
Figure 3B:
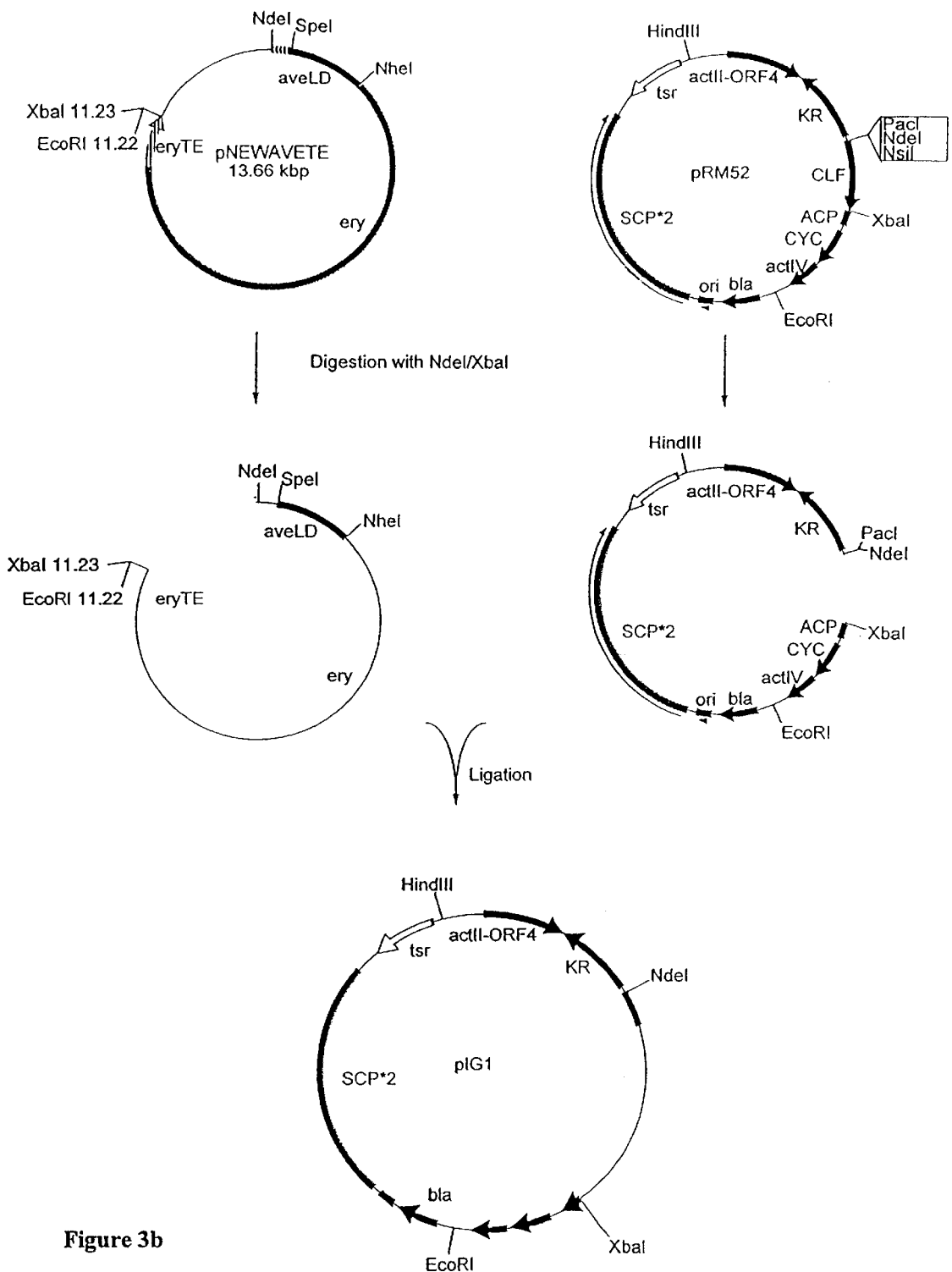

Plasmid pIG1 consists of an SCP2*-derived plasmid containing a hybrid Type I PKS gene comprising the avr loading module in place of the ery loading module, the first two extension modules of the ery PKS and the thioesterase of the ery PKS. This is constructed via several intermediate plasmids as follows (FIG. 3).

(i) Construction of Plasmid pVE3.4

Plasmid pVE1446 which contains a portion of the avermectin (avr) PKS genes was obtained from E. coli strain ATCC 68250 (MacNeil, D. J. et al. Ann. N. Y. Acad. Sci. (1994) 721:123–132). Plasmid pVE1446 was digested with BamHI and the 7.6 kbp fragment between coordinates 32.15 and 3.40 (MacNeil, D. J. et al. Ann. N. Y. Acad. Sci. (1994) 721:123–132) was purified by gel electrophoresis and recircularised. The mixture contained the desired plasmid pVE3.4 which was isolated after transformation of E. coli strain TG1recO (constructed by Dr. P Oliver, Dept. of Genetics, U. Cambridge; Kolodner, R. et al. J. Bacteriol. (1985) 163: 1060–1066; T. Gibson, Ph.D. Thesis, U. Cambridge, 1985.

(ii) Construction of Plasmid pNCO12

Plasmid pBK25 (Bevitt, D. J. et al. Eur. J. Biochem. (1992) 204:39–49) was digested with NcoI and the 12 kbp fragment was end-repaired and ligated into plasmid pUC18 which had been linearised with SmaI. The ligation mixture was transformed into E. coli TG1 recO and individual colonies were checked for their plasmid content. The desired plasmid pNCO12 was identified by its restriction pattern.

(iii) Construction of Plasmid pCRabc

Plasmid pCRabc (FIG. 3) was constructed as follows. Three separate PCR reactions were conducted: First, 20 pmol each of synthetic oligonucleotides A1 (5'-CTCGTCGGT GGCTTT GCG-3') and A2 (5'-CCC GGG AAA AAC GAA GAC TAG TGG CGC GGA CGG CCG-3') were used to amplify a 1.0 kbp product from 100 ng pNCO12 template. The PCR product was end-repaired, phosphorylated and cloned into SmaI-cut pUC18 to obtain plasmid pCRa. Secondly, 20 pmol each of synthetic oligo- nucleotides C1 (5'-CAC GCG CAG CGC GGC GGA-3') and C2 (5'-CGAA CCG CTA GCG GTC GTC GCG ATG GCCT-3') were used to amplify a 1.5 kbp product from 100 ng pNC012 template. The product was end-repaired, phosphorylated and cloned into SmaI-cut pUC18 to obtain plasmid pCRc. Thirdly, 20 pmol each of synthetic oligonucle- otides B1 (5'-GTGGCCCGGCCGTCCGCGCCACTAGTC TTCGTTTTT-3') and B2 (5'-AACAGCTAGCGGTTC GTCCGCCGCTGCCGTGCC-3') were used to amplify a 1.4 kbp product from 100 ng pVE3.4 template. The product was end-repaired, phosphorylated and cloned into SmaI-cut pUC18 to obtain plasmid pCRb.

Plasmid pCRa was digested with HindIII and SpeI and the 1.0 kbp insert was ligated with plasmid pCRb previously digested with HindIII and SpeI, to obtain plasmid pCRab. Plasmid pCRc was digested with NheI and EcoR1 and the 1.5 kbp insert was ligated with plasmid pCRab previously digested with NheI and EcoR1 to obtain plasmid pCRabc.

(iv) Construction of Plasmid pNEWAVETE

Plasmid pCRabc was digested with MfeI and SfiI and the DNA fragment containing the loading domain of the avr PKS was purified by gel electrophoresis and ligated with plasmid pNTEP2 which had been digested with MfeI and SfiI and the larger fragment purified by gel electrophoresis. The ligation mixture was transformed into E. coli TG1 recO and individual colonies were checked for their plasmid content. The desired plasmid pNEWAVETE (13.7 kbp) was identified by its restriction pattern.

(v) Construction of Plasmid pRM52

Plasmid pRM52 is a derivative of plasmid pRM5 (McDaniel, R. et al. Science, (1993) 262:1546–1550). pRM5 was first linearised by digestion with NdeI, end-repaired and then religated to produce pRM51. pRM51 was cut with PacI and NsiI and the large PacI-NsiI fragment was isolated and ligated to a short double-stranded oligonucle- otide linker containing an NdeI site and constructed from the synthetic oligonucleotides 5'-TAAGGAGGACACA TATGCA-3' and 5'-TAATTCCTCCTGTGTAT-3' which were annealed together. The ligation mixture was trans- formed into E. coli TG1recO and isolated colonies were screened for their plasmid content. The desired plasmid (19.6 kbp) was identified by its restriction map and was designated pRM52.

(vi) Construction of Plasmid pIG1

Plasmid pNEWAVETE was digested with NdeI and XbaI and the insert was purified by sedimentation on a sucrose gradient. The purified insert was ligated into plasmid pRM52 (19.6 kbp) which had been digested with NdeI and XbaI, and the vector purified by sedimentation on a sucrose gradient. The ligation mixture was used to transform *E. coli* and individual colonies were checked for their plasmid content. The desired plasmid pIG1 was identified by its restriction pattern.

EXAMPLE 1b

Construction of Plasmid pND30

Plasmid pND30 consists of an SCP2*-derived plasmid containing a hybrid Type I PKS gene comprising the avr loading module in place of the ery loading module, the first two extension modules of the ery PKS and the thioesterase of the ery PKS. This is constructed via several intermediate plasmids as follows (FIG. 4).

(i) Construction of the Recombinant Vector pCJR101 pCJR101 (FIG. 4) is a shuttle plasmid constructed to be used for expression of PKS genes in actinomycetes. It includes a ColE1 replicon to allow it to replicate in *E. coli*, an SCP2*low copy number Streptomyces replicon (Bibb, M. J. and Hopwood, D. A. J. Gen. Microbiol. (1981) 126:427) and the actII-orf4 activator gene from the act cluster which activates transcription from the act promoter during the transition from growth phase to stationary phase in the vegetative mycelium. It is constructed as follows: an approximately 970 bp DNA fragment from pMF1015 (containing the actIIorf4 activator gene) (Fernandez-Moreno, M. A. et al. Cell (1991) 66:769–780) is amplified by PCR, using as primers the synthetic oligonucleotides: 5'-ACT AGT CCA CTG CCT CTC GGT AAA ATC AGC-3' and 5'-CTT AAG AGG GGC TCC ACC GCG TTC ACG GAC-3', which also introduces flanking SpeI and AflIII restriction sites. This fragment is cloned into the end-repaired AatII site of plasmid pUC19 to yield plasmid pCJR18. An approximately 215 bp DNA fragment is amplified from pMV400 which contains the bidirectional promoter pair PactIII/PactI) (Parro, V. et al. Nucl. Acids Res. (1991) 19:2623–2627), using as primers the synthetic oligonucleotides 5'-ACA TTC TCT ACG CCT AAG TGT TCC CCT CCC TGC CTC-3' and 5'-GTG ATG TAT GCT CAT ATG TGT CCT CCT TAA TTA ATC GAT GCG TTC GTC CGG TG-3', which also introduces flanking NdeI and AflIII sites. The PCR product is digested with NdeI and AflIII and ligated with the plasmid pCJR18 previously cut with NdeI and AflIII, to generate plasmid pCJR19. A 1.1 kbp HindIII SphI fragment containing the tsr gene, which confers resistance to thiostrepton, is obtained by PCR from plasmid plJ922 (Lydiate, D. J. et al. Gene (1985) 35:223–235) as template, using as primers the oligonucleotides 5'-TGA ACA CCA AGC TTG CCA GAG AGC GAC GAC TTC CCC-3' and 5'-GAC AGA TTG CAT GCC CTT CGA GGA GTG CCC GCC CGG-3' which also introduces flanking HindIII and SphI sites. The PCR product is digested with HindIII and SphI and ligated with plasmid pCJR19 cut with HindIII and SphI to obtain plasmid pCJR24. The plasmid plJ922 is digested with BamHI and SstI and the fragment containing a portion of the fertility locus and the origin of replication (Lydiate, D. J. et al. Gene (1985) 35:223–235) is ligated into pUC19 digested with BamHI and SstI to generate the bifunctional plasmid pCJR16 (14.7 kbp). Plasmid pCJR24 is digested with SalI and SphI, the two larger fragments from the digest are purified by gel electrophoresis, and combined in a four-component ligation with plasmid pCJR16 which has been digested with XhoI and SphI. The ligation mixture is used to transform Streptomyces lividans and colonies are selected in the presence of thiostrepton. One such colony is shown to contain the desired plasmid pCJR101 (approx. 12.4 kbp), identified by its restriction pattern.

(ii) Construction of Plasmid pCJR29

Figure 4A:
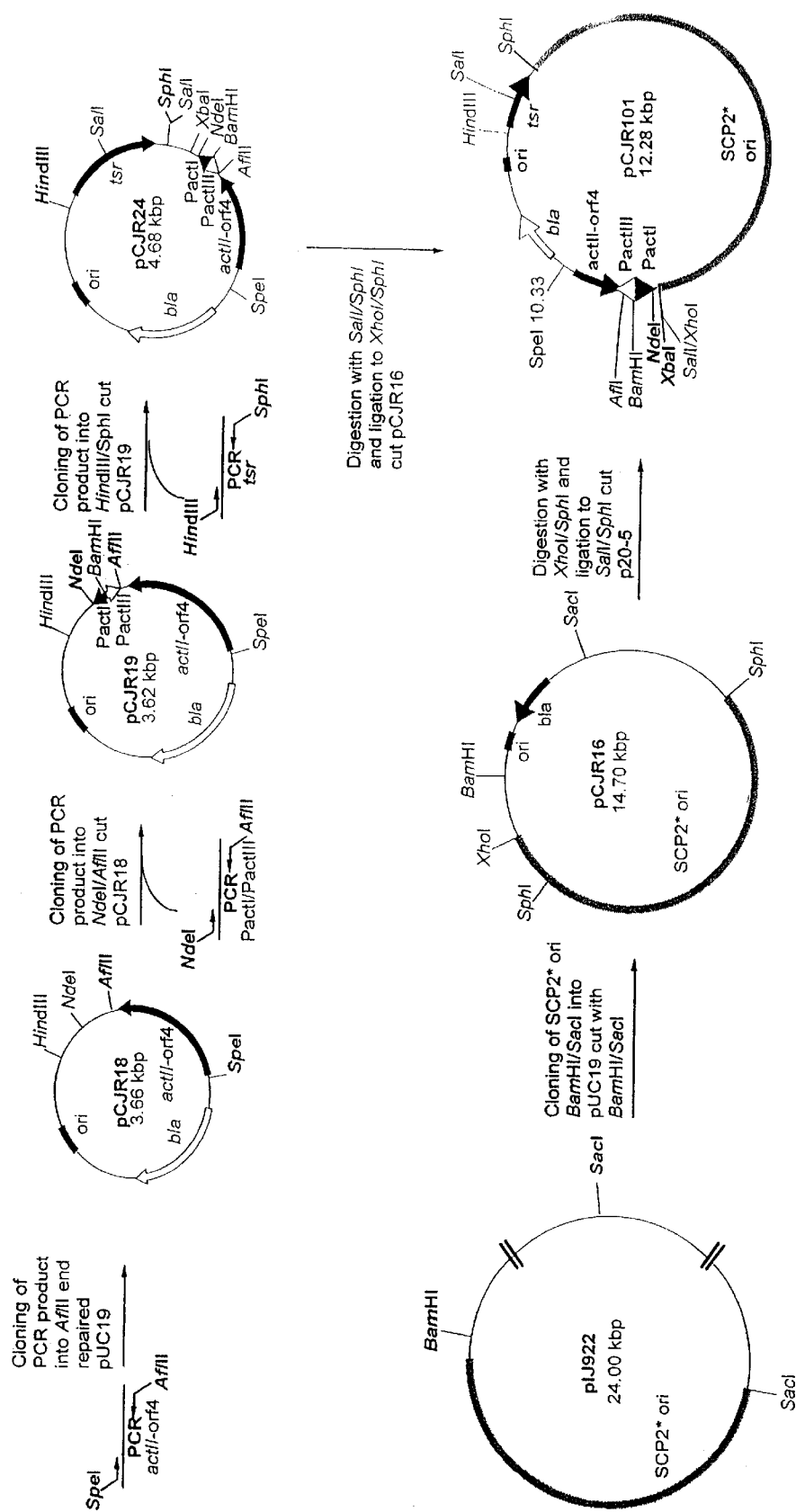
FIGS. 4a, 4b, and 4c are diagrams showing the construction of plasmid pND30.
Figure 4B:
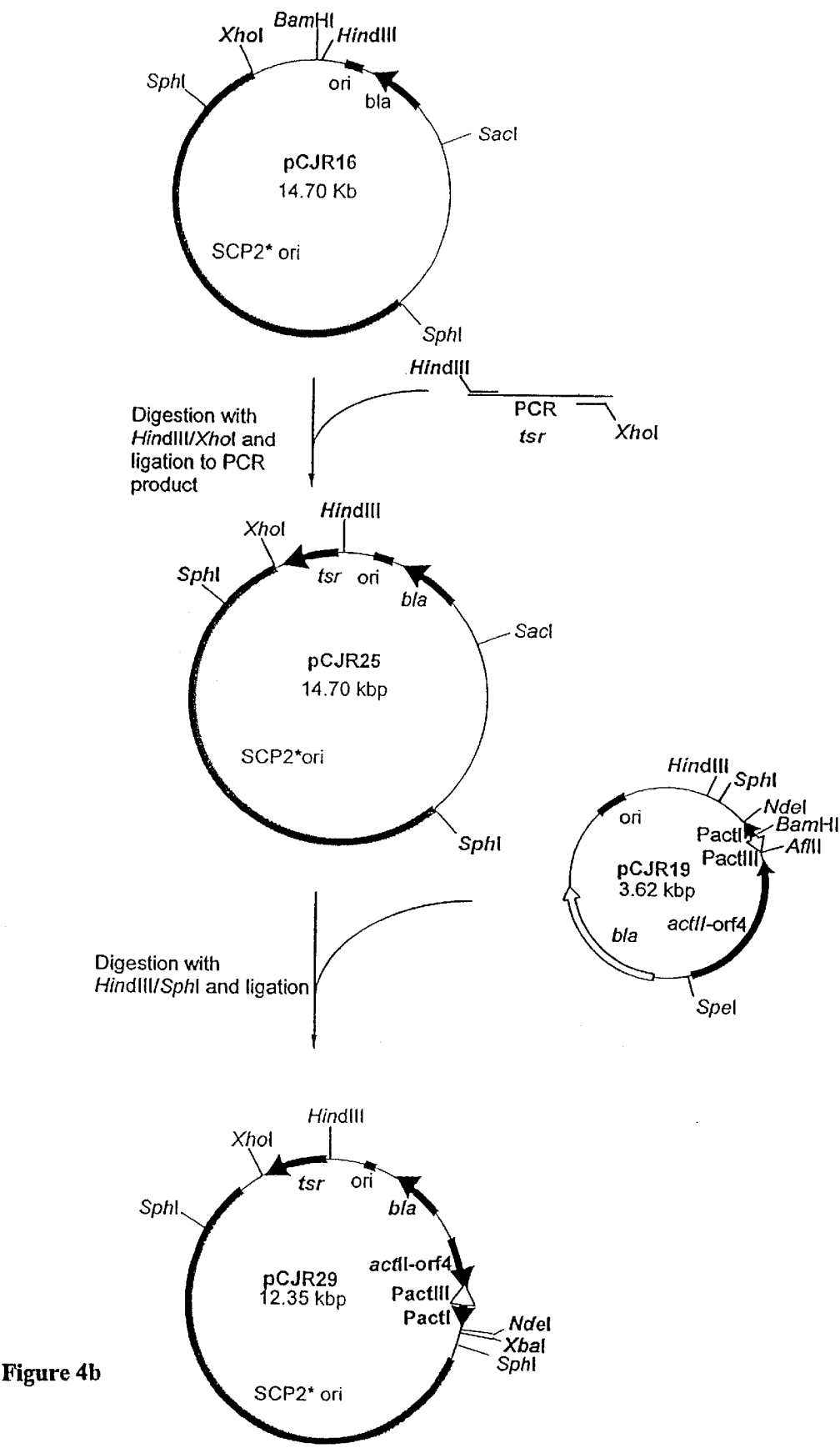
Figure 4C:
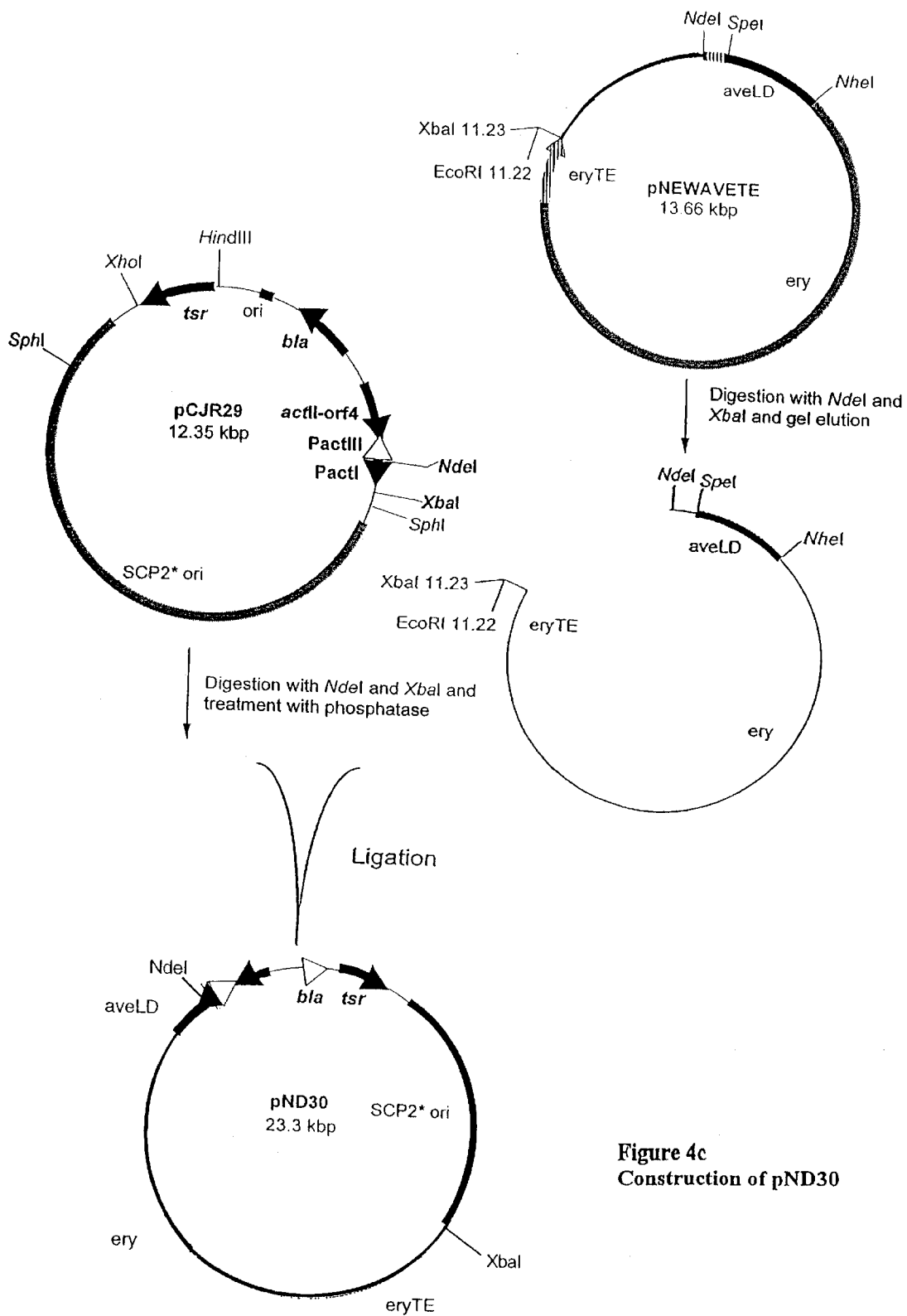

The construction of plasmid pCJR29 is illustrated in FIG. 4. A 1.1 kbp HindIII-XhoI fragment containing the tsr gene, which confers resistance to thiostrepton, is obtained by PCR from plasmid plJ922 as template, using as primers the oligonucleotides 5'-TGA ACA CCA AGC TTG CCA GAG AGC GAC GAC TTC CCC 3' and 5'-GAC AGA TTC TCG AGC CTT CGA GGA GTG CCC GCC CGG-3' which also introduces flanking HindIII and XhoI sites. The PCR product is digested with HindIII and XhoI and ligated with plasmid pCJR16 which has been digested with HindIII and XhoI, to generate plasmid pCJR25. Plasmid pCJR25 is digested with HindIII and SphI and ligated with plasmid pCJR19 which has been digested with HindIII and SphI, to produce the desired plasmid pCJR29 (approx. 12.4 kbp), identified by its restriction pattern. Plasmid pCJR29 differs from pCJR101 in the orientation of the tsr gene, the actII-orf4 gene and the actI/actIII promoter, with respect to the SCP2*-derived origin of replication.

(iii) Construction of Plasmid pND30

Plasmid pNEWAVETE was digested with NdeI and XbaI and the insert was purified by sedimentation on a sucrose gradient. The purified insert was ligated into plasmid pCJR29 (approx. 12.4 kbp) which had been digested with NdeI and XbaI, and the vector purified by sedimentation on a sucrose gradient. The ligation mixture was used to transform *E. coli* and individual colonies were checked for their plasmid content. The desired plasmid pND30 was identified by its restriction pattern.

EXAMPLE 1c

Construction of Plasmid pCJR26

Figure 8:
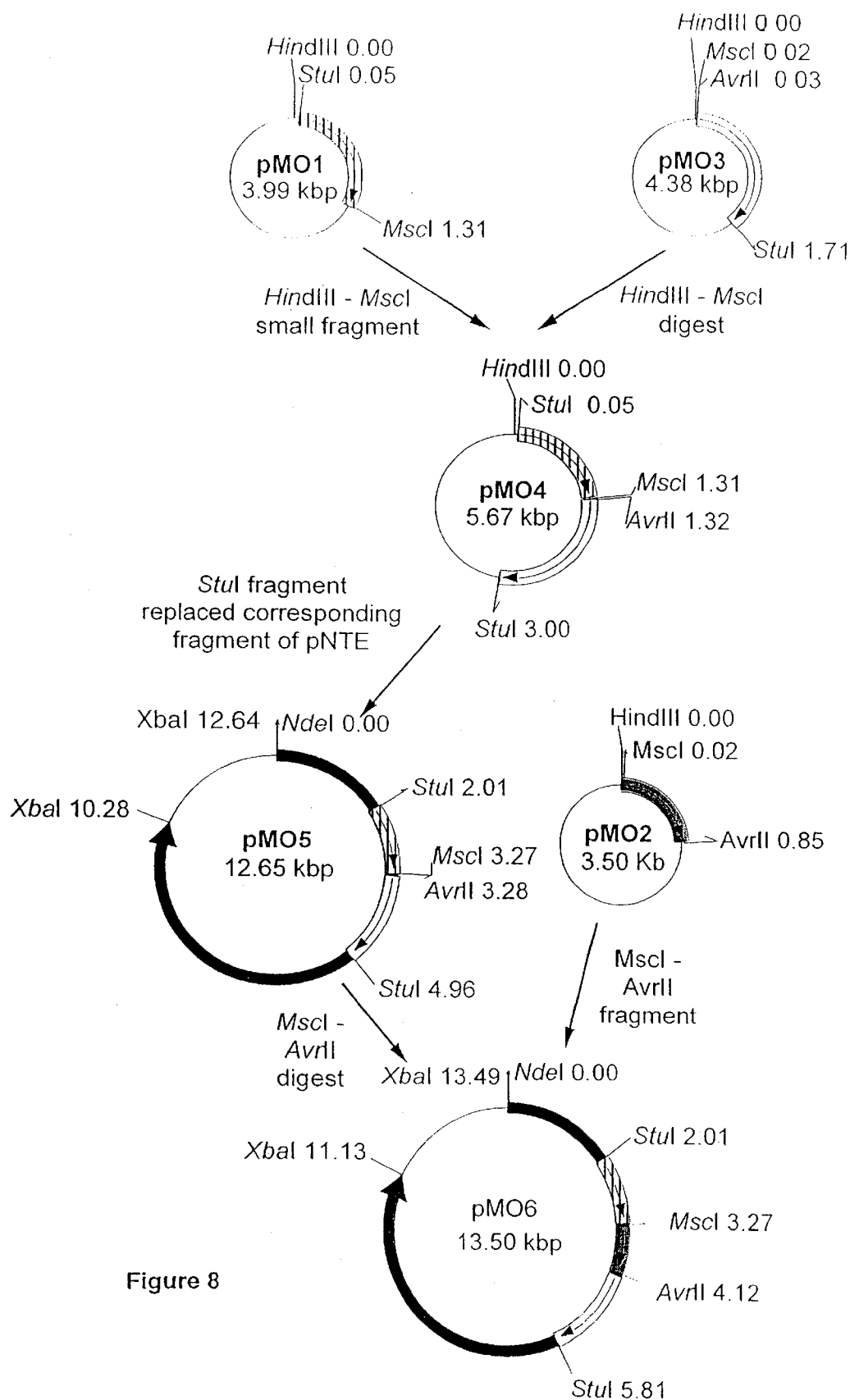
FIG. 8 is a diagram showing the construction of plasmid pMO6.

Plasmid pMO6 (FIG. 8) was first constructed in several steps:

(i) Construction of plasmid pMO1

The approximately 1.3 kbp DNA segment of the eryAI gene of *S. erythraea* extending from nucleotide 1948 to nucleotide 3273 of eryAI (Donadio. S. et al., Science (1991) 252, 675–679) was amplified by PCR employing as primers synthetic oligonucleotides: 5'-CAT GCT CGA GCT CTC CTG GGA AGT-3' and 5'-CAA CCC TGG CCA GGG AAG ACG AAG ACG G-3', and plasmid pNTEP2 as a template. The PCR product was end-repaired and ligated with plasmid pUC18, which had been linearised by digestion with SmaI and then treated with alkaline phosphatase. The ligation mixture was used to transform *E. coli* TG1 recO and individual colonies were checked for their plasmid content. The desired plasmid pMO1 (3.9 kbp), in which the StuI site bordering the insert is adjacent to the HindIII site in the polylinker, was identified by its restriction pattern.

(ii) Construction of Plasmid pMO2

The approximately 0.85 kbp DNA segment of the rapA gene of *Streptomyces hygroscopicus*, extending from nucleotide 1643 to nucleotide 2486 of rapA, was amplified by PCR employing as primers the following oligonucleotides: 5'-TTC CCT GGC CAG GGG TCG CAG CGT G-3' and 5'-CAC CTA GGA CCG CGG ACC ACT CGA C-3', and the DNA from the recombinant bacteriophage λ-1E (Schwecke, T. et al., Proc. Natl. Acad. Sci. USA (1995) 92:7839–7843) as the template. PCR product was end-repaired and ligated with plasmid pUC18, which had been linearised by digestion with SmaI and then treated with alkaline phosphatase. The ligation mixture was used to transform *E. coli* TGI recO and individual colonies were checked for their plasmid content. The desired plasmid pMO2 (3.5 kbp) was identified by its restriction pattern.

(iii) Construction of Plasmid pMO3

The approximately 1.7 kbp DNA segment of the eryAI gene of *S. erythraea* extending from nucleotide 4128 to nucleotide 5928 of eryAI, was amplified by PCR employing as primers the synthetic oligonucleotides: 5'-TGG CCA GGG AGT CGG TGC ACC TAG GCA-3' and 5'-GCC GAC AGC GAG TCG ACG CCG AGT T-3', and plasmid pNTEP2 as template. The PCR product was end-repaired and ligated with plasmid pUC18, which had been linearised by digestion with SmaI and then treated with alkaline phosphatase. The ligation mixture was used to transform *E. coli* TG1 recO and individual colonies were checked for their plasmid content. The desired plasmid pMO3 (4.4 kbp), in which BalI and AvrII sites are adjacent to the HindIII site of the polylinker, was identified by its restriction pattern.

(iv) Construction of Plasmid pMO4

Plasmid pMO1 was digested with HindIII and BalI and the 1.3 kbp insert was ligated with plasmid pMO3 which had been digested with HindIII and BalI. The ligation mixture was used to transform *E. coli* TG1 recO and individual colonies were checked for their plasmid content. The desired plasmid pMO4 (5.6 kbp) was identified by its restriction pattern.

(v) Construction of Plasmid pMO5

Plasmid pMO4 was digested with StuI and the 3.0 kbp insert was ligated with plasmid pNTEP2 which had been digested with StuI and purified by gel electrophoresis to remove the 3.8 kbp insert. The ligation mixture was transformed into *E. coli* TG1 recO and individual colonies were checked for their plasmid content. The plasmid pMO5 (12.8 kbp) was identified by its restriction pattern.

(vi) Construction of Plasmid pMO6

Plasmid pMO2 was digested with BalI and AvrII and the insert was ligated with plasmid pMO5 which had been digested with BalI and AvrII. The ligation mixture was used to transform *E. coli* TG1 recO and individual colonies were checked for their plasmid content. The desired plasmid pMO6 (13.5 kbp) was identified by its restriction pattern.

(vii) Construction of Plasmid pCJR26

Figure 9:
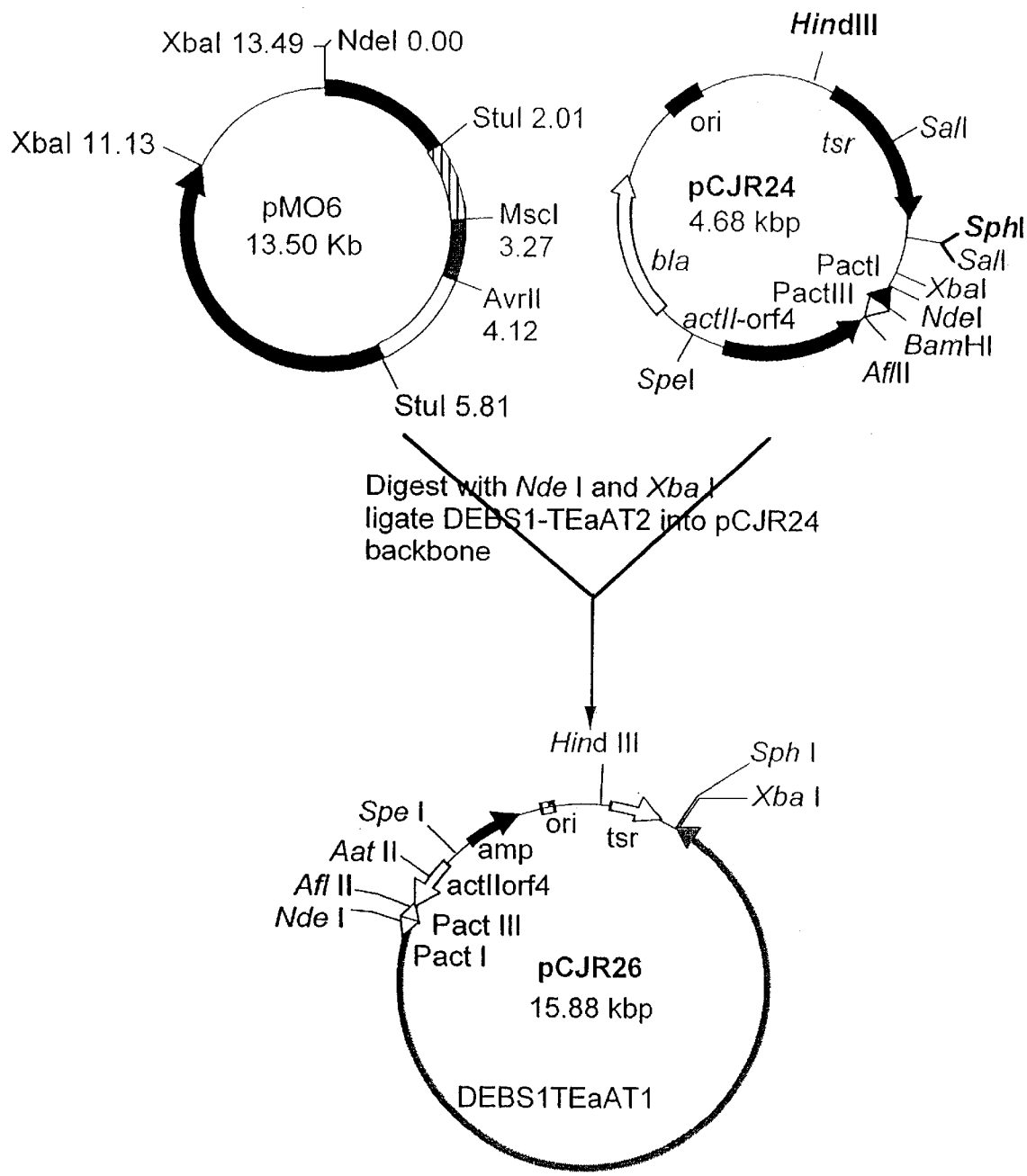
FIG. 9 is a diagram showing the construction of plasmid pCJR26.

Plasmid pCJR26 is an SCP2*based plasmid containing a PKS gene comprising the ery loading module, the first and second extension modules of the ery PKS and the ery chain-terminating thioesterase, except that the DNA segment encoding the methylmalonyl-CoA:ACP acyltransferase within the first extension module has been specifically substituted by the DNA encoding the malonyl-CoA-ACP acyltransferase of module 2 of the rap PKS. It was constructed as follows (FIG. 9): plasmid pMO6 was digested with NdeI and XbaI and the insert was ligated with plasmid pCJR24, which had been digested with NdeI and XbaI and purified by gel electrophoresis. The ligation mixture was transformed into *E. coli* TG1 recO and individual colonies were checked for their plasmid content. The desired plasmid pCJR26 was identified by its restriction pattern.

EXAMPLE 1d

Construction of *S. erythraea* JC2/pCJR26 and Production of TKL Derivatives

Plasmid pCJR26 was used to transform *S. erythraea* JC2 protoplasts. Thiostrepton resistant colonies were selected on R2T20 medium containing 10 μg/ml of thiostrepton. Several clones were tested for the presence of pCJR26 integrated into the chromosome by Southern blot hybridisation of their genomic DNA with DIG-labelled DEBS1-TE gene.

A clone with an integrated copy of pCJR26 was grown in SSM medium, containing 5 μg/ml of thiostrepton and allowed to grow for seven days at 28–30° C. After this time the broth was filtered to remove mycelia and the pH was adjusted to pH 3. The broth was extracted twice with two volumes of ethyl acetate and the combined ethyl acetate extracts were washed with an equal volume of saturated sodium chloride, dried over anhydrous sodium sulfate, and the ethyl acetate was removed under reduced pressure, to give about 500 mg of crude product. The products were shown to be (2S, 3R, 5R)-2-methyl-3,5-dihydroxy-n-hexanoic acid δ-lactone and (2S, 3R, 5R)-2-methyl-3,5-dihydroxy-n-heptanoic acid δ-lactone:

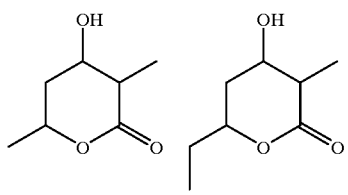

EXAMPLE 1e

Construction of *S. erythraea* NRRL 2338/pCJR26 and its use in Production of 14-membered Macrolides Approximately 5 mg pCJR49 DNA was used to transform *S. erythraea* NRRL2338 protoplasts to give a strain in which the plasmid is integrated into the chromosome. From several colonies, total DNA was obtained and analysed by Southern hybridisation to confirm that the plasmid has integrated in module 2 of EryAI to give a novel macrolide biosynthetic pathway. Further integrations had occurred to give repeated plasmid sequences. *S. erythraea* NRRL 2338/pCJR49 was inoculated into tryptic soy broth containing 5 mg/ml thiostrepton and incubated at 30° C. for three days. 100 mL of this seed culture was used to inoculate 2 L of sucrose succinate defined medium containing 5 mg/mL thiostrepton in 5×2 L flasks each containing 500 mL medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC/MS and two macrolides were identified as the erythromycin analogues:

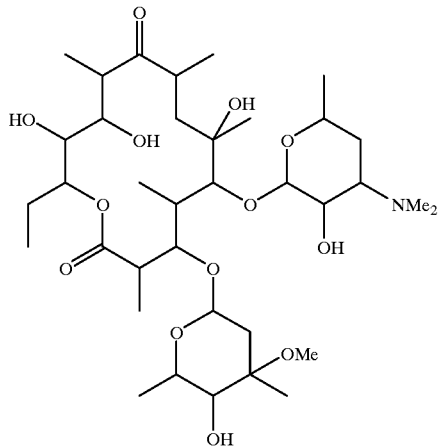

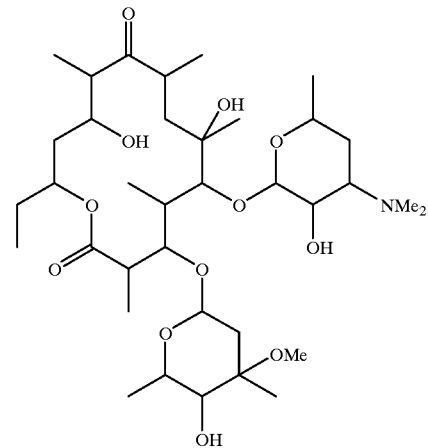

EXAMPLE 1f

Construction of Plasmid pC-ATX

Figure 10:
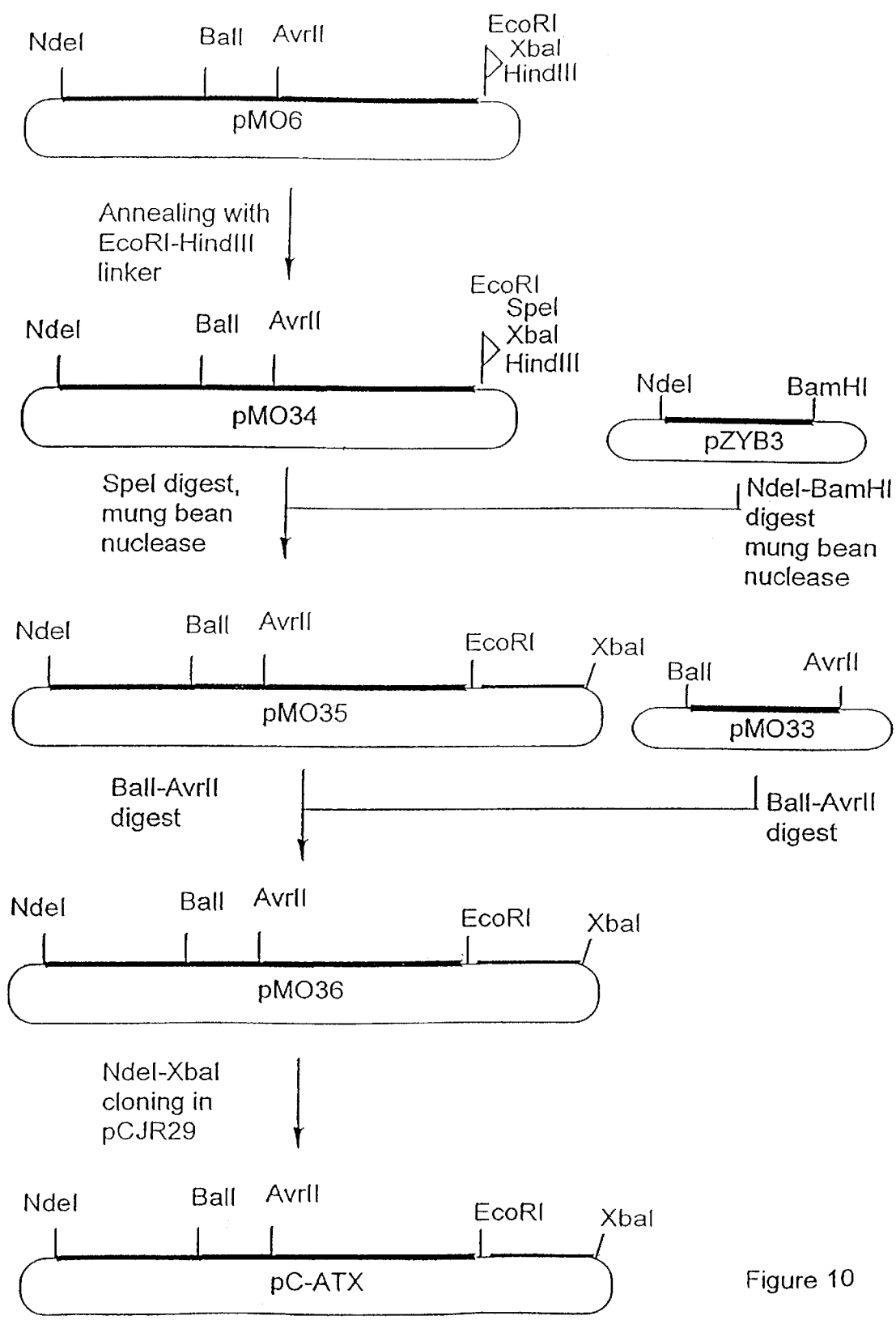
FIG. 10 is a diagram showing the construction of plasmid pC-ATX.

Plasmid pC-ATX is an SCP2* based plasmid containing a PKS gene comprising the ery loading module, the first and second extension modules of the ery PKS and the ery chain-terminating thioesterase, except that the DNA segment encoding the methylmalonyl-CoA:ACP acyltransferase within the first extension module has been specifically substituted by the DNA encoding the malonyl-CoA:ACP acyltransferase from a putative type I PKS gene cluster cloned from *Streptomyces cinnamonensis* ATCC 14513 (producer of the polyether polyketide monensin). It was constructed via several intermediate plasmids as follows (FIG. 10).

(i) Isolation of Cosmid pSCIN02

Genomic library of *Streptomyces cinnamonensis* ATCC 14513 (the monensin producer) was constructed from size fractioned 35–45 kbp Sau3A fragments of chromosomal DNA ligated into BamHI-linearised and alkaline phosphatase-treated cosmid vector pWE15. The ligation mixture was packaged into λ-particles using Gigapack packaging extracts, and transfected into *E. coli* NM1blue. Approximately 600 colonies of the library were grown on the surface of a nylon membrane, lysed, and their DNA was crosslinked to the membrane by UV irradiation. The membrane was subsequently used for the screening procedure. The insert of pMO8 comprising the ketosynthase domain from module 2 of DEBS was labelled by random priming in the presence of $^{33}$P αATP and used as a probe for DNA hybridisation. The probe was hybridised for 16 h at 68° C. in 4.0×SSC buffer and subsequently washed off for 1 h at 68° C. in 0.8×SSC buffer. Three positive clones were isolated. DNA of the inserts of all three clones was end sequenced from T3 and T7 priming sites present in the vector pWE15. A region homologous to type I ketosynthase and malonyl-CoA:ACP acyltransferase domains was discovered in the DNA sequence from the T7 priming site using clone 2 (named pSCIN02) as a template. Partial DNA sequencing of the malonyl-COA:ACP acyltransferase domain (named ATX) revealed an unusual sequence motif in the putative substrate recognition part of the domain which was substantially different from previously described malonate- or methylmalonate-specific CoA:ACP acyltransferases (Haydock, S. F. et al., FEBS (1995) 374–246–248)

(ii) Construction of Plasmid pMO38

The approximately 0.9 kbp DNA segment of the ATX domain was amplified by PCR employing as primers the following oligonucleotides 5'-CTG GCC AGG GCG CGC AAT GGC CGA GCA T-3' and 5'-CCC TAG GAG TCG CCG GCA GTC CAG CGC GGC GCC C-3' using the DNA from the cosmid pSCIN02 as the template. The PCR product was end-repaired and ligated with plasmid pUC18, which had been linearised by digestion with SmaI and then treated with alkaline phosphatase. The ligation mixture was used to transform *E. coli* TGI recO and individual colonies were checked for their plasmid content. The desired plasmid pMO38 (3.5 kbp) was identified by its restriction pattern.

(iii) Construction of Plasmid pMO34

Plasmid pMO34 is a derivative of pMO6 with a polycloning site inserted after the stop codon of the inserted D1-AT2 gene. Plasmid pMO6 was digested with EcoRI and HindIII and annealed with two oligonucleotides forming the double-stranded region of the polycloning site: 5'-AAT TCA TAA CTA GTA GGA GGT CTG GCC ATC TAG A-3' and 5'-TCG AAG ATC TAC CGG TCT GGA GGA TGA TCA ATA C-3'. The mixture was ligated and transformed into *E. coli* TGI recO. Individual colonies were checked for their plasmid content. The desired plasmid pMO34 (13.5 kbp) was identified by its restriction pattern.

(iv) Construction of Plasmid pMO35

Plasmid pMO35 is a derivative of pMO34 containing TKLS-AT2 gene and a translationally coupled crotonyl-CoA-reductase gene from *Streptomyces collinus* (Wallace et al., E. J. Biochem. (1995) 233: 954–962). The crotonyl-CoA-reductase gene was excised from the plasmid pZYB3 (the gift of Prof. K. Reynolds) as an NdeI-BamHI fragment, which was treated with mung bean nuclease to produce blunt ends and ligated into pMO34 previously cut with SpeI and likewise blunt-ended using mung bean nuclease. The ligation mixture was used to transform *E. coli* TG1 recO and individual colonies were checked for their plasmid content. The desired plasmid pMO35 (14.2 kbp), with the correct orientation of the crotonyl-CoA-ketoreductase gene, was identified by its restriction pattern.

(v) Construction of Plasmid pMO36

Plasmid pMO38 was digested with BalI and AvrII and the insert was ligated with plasmid pMO35 which had been digested with BalI and AvrII. The ligation mixture was used to transform *E. coli* TG1 recO and individual colonies were checked fon their plasmid content. The desired plasmid pMO36 (13.5 kbp) was identified by its restriction pattern.

(vi) Construction of Plasmid pC-ATX

Plasmid pMO36 was digested with NdeI and XbaI and the insert was ligated with plasmid pCJR29, which had been digested with NdeI and XbaI and purified by gel electrophoresis. The ligation mixture was transformed into *E. coli* TG1 recO and individual colonies were checked for their plasmid content. The desired plasmid pC-ATX was identified by its restriction pattern.

EXAMPLE 1g

Construction of *S. erythraea* JC2/pC-ATX and Production of TKL Derivatives

Plasmid pC-ATX was used to transform *S. erythraea* JC2 protoplasts. Thiostrepton resistant colonies were selected on R2T20 medium containing 10 μg/ml of thiostrepton. Several clones were tested for presence of pC-ATX integrated into the chromosome by Southern blot hybridisation of their genomic DNA with DIG-labelled DNA encoding the DEBS1-TE gene.

A clone with an integrated copy of pC-ATX was grown in SSM medium, containing 5 μg/ml of thiostrepton, and allowed to grow for seven days at 28–30° C. After this time the broth was filtered to remove mycelia and the pH adjusted to pH 3. The broth was extracted twice with two volumes of ethyl acetate and the combined ethyl acetate extracts were washed with an equal volume of saturated sodium chloride, dried over anhydrous sodium sulfate, and the ethyl acetate was removed under reduced pressure, to give about 500 mg of crude product. The products were characterised by gas chromatography, mass spectrometry and NMR, and were shown to be (2S, 3R, 4S, 5R)-2-methyl-4-ethyl-3,5-dihydroxy-n-hexanoic acid δ-lactone and (2S, 3R, 4S, 5R)-2-methyl-4-ethyl-3,5-dihydroxy-n-heptanoic acid δ-lactone:

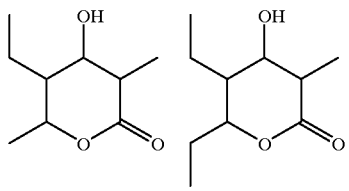

EXAMPLE 1h

Construction of *S. erythraea* NRRL 2338/pC-ATX and its use in Production of 14-membered Macrolides Approximately 5 mg pC-ATX DNA was used to transform *S. erythraea* NRRL 2338 protoplasts to give a strain in which the plasmid is integrated into the chromosome. From several colonies, total DNA was obtained and analysed by Southern hybridisation to confirm that the plasmid has integrated in module 2 of EryAI to give a novel macrolide biosynthetic pathway. Further integrations had occurred to give repeated plasmid sequences. *S. erythraea* NRRL 2338/ pC-ATX was inoculated into tryptic soy broth containing 5 mg/mL thiostrepton and incubated at 30° C. for three days. 100 mL of this seed culture was used to inoculate 2 L of sucrose succinate defined medium containing 5 mg/mL thiostrepton in 5×2 L flasks each containing 500 mL medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC-MS and two macrolide products were identified:

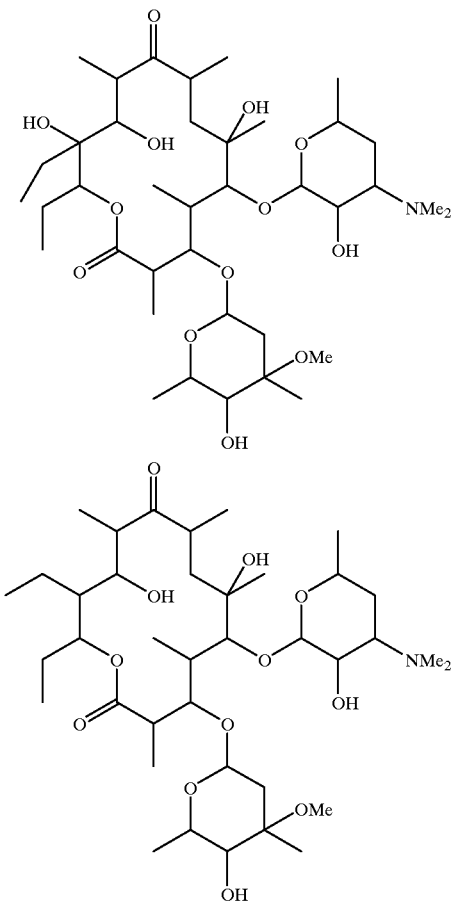

EXAMPLE 1i

Construction of Plasmid pC-AT12

Figure 11:
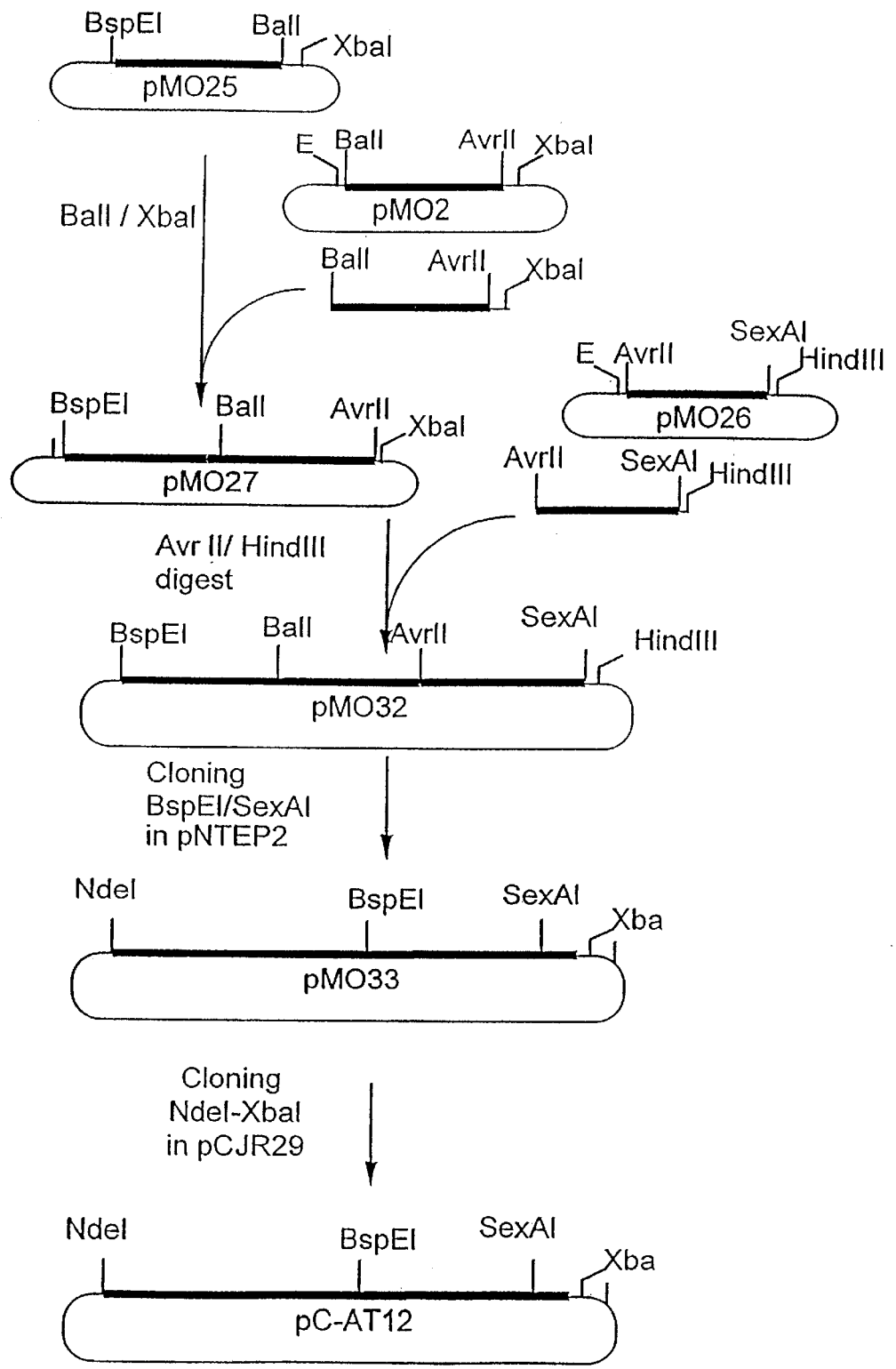
FIG. 11 is a diagram showing the construction of plasmid pC-AT12.

Plasmid pC-AT12 is an SCP2* based plasmid containing a PKS gene comprising the ery loading module, the first and second extension modules of the ery PKS and the ery chain-terminating thioesterase, except that the DNA segment encoding the methylmalonyl-CoA:ACP acyltransferase within the second extension module has been specifically substituted by the DNA encoding the malonyl-CoA:ACP acyltransferase of module 2 of the rap PKS. It was constructed via several intermediate plasmids as follows (FIG. 11).

(i) Construction of Plasmid pMO25

The approximately 1.0 kbp DNA segment of the eryAI gene of *S. erythraea* extending from nucleotide 6696 to nucleotide 7707 of eryAI (Donadio. S. et al., Science (1991) 252, 675–679) was amplified by PCR employing as primers synthetic oligonucleotides: 5'-GGC GGG TCC GGA GGT GTT CAC CGA GTT-3' and 5'-ACC TTG GCC AGG GAA GAC GAA CAC TGA-3', and plasmid pNTEp2 as a template. The PCR product was end-repaired and ligated with plasmid pUC18, which had been linearised by digestion with SmaI and then treated with alkaline phosphatase. The ligation mixture was used to transform *E. coli* TG1recO and individual colonies were checked for their plasmid content. The desired plasmid pMO25 (3.6 kbp), in which the StuI site bordering the insert is adjacent to the HindIII site in the polylinker, was identified by its restriction pattern.

(ii) Construction of Plasmid pMO26

The approximately 0.6 kbp DNA segment of the eryAI gene of *S. erythraea* extending from nucleotlde 8660 to nucleotide 9258 of eryAI, was amplified by PCR employing as primers the synthetic oligonucleotides: 5'-TCC TAG GCC GGG CCG GAC TGG TCG ACC TGC CGG GTT-3' and 5'-AAA CAC CGC GAC CTG GTC CTC CGA GC-3', and plasmid pNTEP2 as template. The PCR product was end-repaired and ligated with plasmid pUC18, which had been linearised by digestion with SmaI and then treated with alkaline phosphatase. The ligation mixture was used to transform *E. coli* TG1recO and individual colonies were checked for their plasmid content. The desired plasmid pMO26 (3.2 kbp), in which the AvrII site is adjacent to the HindIII site of the polylinker, was identified by its restriction pattern.

(iii) Construction of Plasmid pMO27

Plasmid pMO25 was digested with EcoRI and BalI and the 1.0 kbp insert was ligated with plasmid pMO2 which had been digested with EcoRI and BalI. The ligation mixture was used to transform *E. coli* TG1recO and individual colonies were checked for their plasmid content. The desired plasmid pMO27 (4.4 kbp) was identified by its restriction pattern.

(iv) Construction of Plasmid pMO32

Plasmid pMO26 was digested with AvrII and HindIII and the 0.6 kbp insert was ligated with plasmid pMO27 which had been digested with AvrII and HindIII. The ligation mixture was used to transform *E. coli* TG1recO and individual colonies were checked for their plasmid content. The desired plasmid pMO32 (5.1 kbp) was identified by its restriction pattern.

(v) Construction of Plasmid pMO33

Plasmid pMO32 was digested with BspEI and SexAI and the 2.7 kbp insert was ligated with plasmid pNTEP2 which had been digested with the same two enzymes and purified by gel electrophoresis to remove the 2.8 kbp insert. The ligation mixture was transformed into *E. coli* TG1recO and individual colonies were checked for their plasmid content. The plasmid pMO33 (12.8 kbp) was identified by its restriction pattern.

(vi) Construction of Plasmid pC-AT12

Plasmid pMO33 was digested with NdeI and XbaI and the insert was ligated with plasmid pCJR29, which had been digested with NdeI and XbaI and purified by gel electrophoresis. The ligation mixture was transformed into *E. coli* TG1recO and individual colonies were checked for their plasmid content. The desired plasmid pC-AT12 was identified by its restriction pattern.

EXAMPLE 1j

Construction of *S. erythraea* JC2/pC-AT12 and Production of TKL Derivatives

Plasmid pC-AT12 was used to transform *S. erythraea* JC2 protoplasts. Thiostrepton resistant colonies were selected on R2T20 medium containing 10 µg/ml of thiostrepton. Several A clone with an integrated copy of pC-AT12 was grown in SSM medium, containing 5 µg/mL of thiostrepton and allowed to grow for seven days at 28–30° C. After this time the broth was filtered to remove mycelia and the pH adjusted to pH 3. The broth was extracted twice with two volumes of ethyl acetate and the combined ethyl acetate extracts were washed with an equal volume of saturated sodium chloride, dried over anhydrous sodium sulfate, and the ethyl acetate was removed under reduced pressure, to give about 500 mg of crude product. The products were shown to be (3R, 4S, 5R)-4-methyl-3,5-dihydroxy-n-hexanoic acid δ-lactone and (3R, 4S, 5R)-4-methyl-3,5-dihydroxy-n-heptanoic acid δ-lactone:

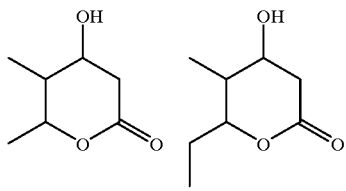

EXAMPLE 1k

Construction of *S. erythraea* NRRL 2338/pC-AT12 and its use in Production of 14-membered Macrolides Approximately 5 µg pC-AT12 DNA was used to transform *S. erythraea* NRRL 2338 protoplasts to give a strain in which the plasmid is integrated into the chromosome. From several colonies, total DNA was obtained and analysed by Southern hybridisation to confirm that the plasmid has integrated 3' of module 2 of EryAI to give a novel macrolide biosynthetic pathway. Further integrations had occurred to give repeated plasmid sequences. *S. erythraea* NRRL 2338/pC-AT12 was inoculated into tryptic soy broth containing 5 mg/mL thiostrepton and incubated at 30° C. for three days. 100 mL of this seed culture was used to inoculate 2 L of sucrose succinate defined medium containing 5 µg/mL thiostrepton in 5×2 L flasks each containing 500 mL medium with 2 springs to aid dispersion and shaken at 300 rpm. After a further 5 days of growth the cultures were centrifuged and the pH of the supernatant adjusted to pH 9. The supernatant was then extracted three times with an equal volume of ethyl acetate and the solvent removed by evaporation. Products were analysed by HPLC-MS and two macrolide products were identified:

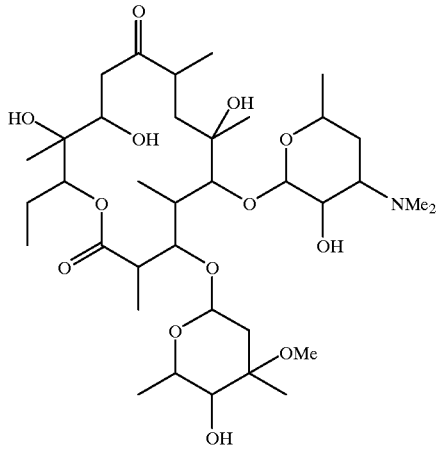

EXAMPLE 11

Figure 12:
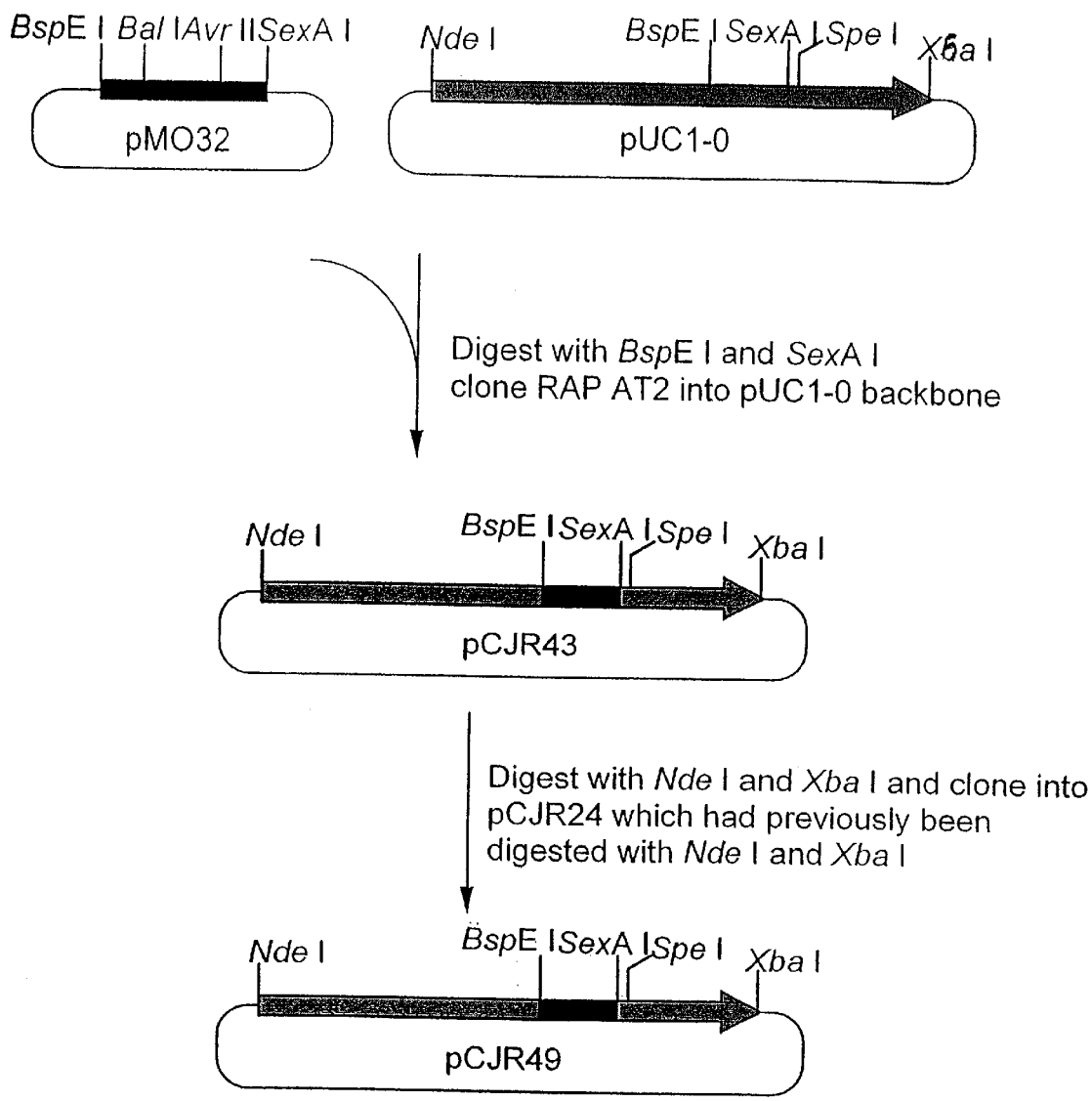
FIG. 12 is a diagram showing the construction of plasmid pCJR49.

Construction of Plasmid pCJR49 pCJR49 is a pCJR24-based plasmid containing a mutant DEBS1-TE gene which has no ketoreductase in module 2, and the AT domain in module 2 has been replaced by RAPS AT2 in order to incorporate a malonyl extender instead of a methylmalonyl extender in the second module (FIG. 12).

pMO32 was digested with BspEl and SexAl and the fragment containing the AT from RAP module 2 was cloned into pUC1–0 which had been previously digested with BspE I and SexA I, to yield the plasmid pCJR43.

pCJR43 was digested with Ndel and Xbal and the fragment containing the mutant DEBS1-TE gene was cloned into pCJR24 which had previously been digested with Ndel and Xbal, to yield plasmid pCJR49. pCJR49 was confirmed by restriction enzyme mapping.

EXAMPLE 1m

Construction of S. erythraea JC2/pCJR49 and Production of TKL Derivatives

Approximately 5 μg pCJR49 DNA was used to transform S. erythraea JC2 protoplasts to give a strain in which the plasmid is integrated into the chromosome. From several colonies total DNA is obtained and analysed by Southern hybridisation to confirm that the plasmid has integrated into the eryTE. S. erythraea JC2/pCJR49 is inoculated into tryptic soy broth containing 5 μg/mL thiostrepton and incubated at 30° C. for three days. 100 mL of this seed culture was used to inoculate 2 L of sucrose succinate defined medium containing 5 μg/mL thiostrepton in 5×2 L flasks each containing 500 mL medium with 2 springs to aid dispersion and shaken at 300 rpm. After a further 5 days of growth the cultures were centrifuged and the pH of the supernatant was adjusted to pH 3. The supernatant was then extracted three times with an equal volume of ethyl acetate and the solvent removed by evaporation. Products were dissolved in methanol and analysed by GCMS on a Finnegan-MAT GCQ System. This analysis indicated that by comparison to synthetic standards two new lactones were present. These products were (4S,5R)-4-methyl-3-keto-5-hydroxyhexanoic acid δ lactone and (4S,5R)-4-methyl-3-keto-5-hydroxyheptanoic acid δ lactone:

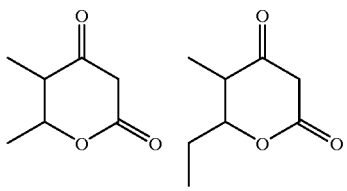

EXAMPLE 1n

Construction of S. erythraea NRRL 2338/pCJR49 and its use for Production of 14-membered Macrolides 5 μg pCJR49 DNA was used to transform S erythraea NRRL 2338 protoplasts to give a strain in which the plasmid is integrated into the chromosome. From several colonies total DNA is obtained and analysed by Southern hybridisation to confirm that the plasmid has integrated in module 2 of EryAI to give a novel macrolide biosynthetic pathway. Further integrations had occurred to give repeated plasmid sequences. S. erythraea/pCJR49 is inoculated into tryptic soy broth containing 5 μg/mL thiostrepton and incubated at 30° C. for three days 100 mL of this seed culture was used to inoculate 2 L of sucrose succinate defined medium containing 5 μug/mL thiostrepton in 5×2 L flasks each containing 500 mL medium with 2 springs to aid dispersion and shaken at 300 rpm. After a further 5 days of growth the cultures were centrifuged and the pH of the supernatant adjusted to pH 9. The supernatant was then extracted three times with and equal volume of ethyl acetate and the solvent removed by evaporation. Products were analysed by HPLC-MS and two macrolides were identified:

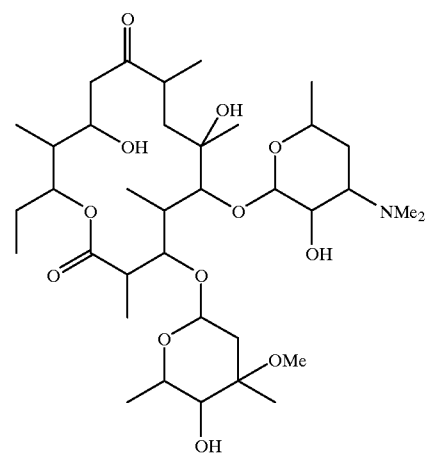

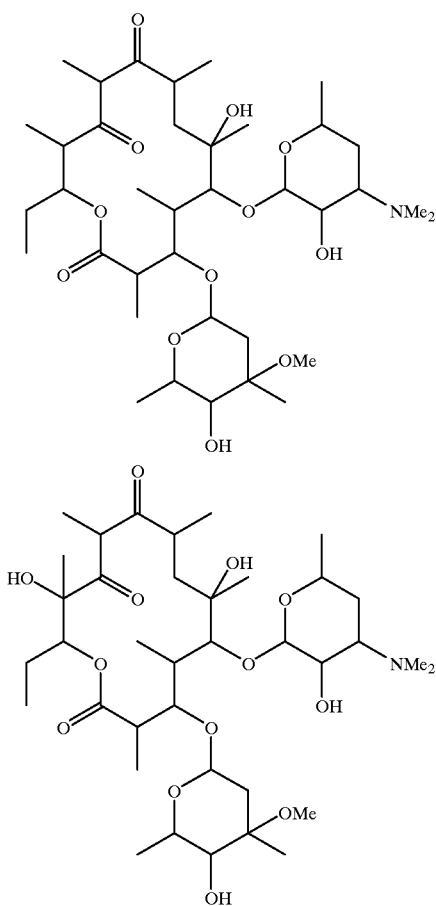

EXAMPLE 2

Construction of S. erythraea ERMD1, Carrying a Hybrid PKS Gene in which the avr Loading Didomain is Substituted for the ery Loading Didomain of S. erythraea NRRL 2338

(i) Construction of Plasmid pAVLD

Figure 5:
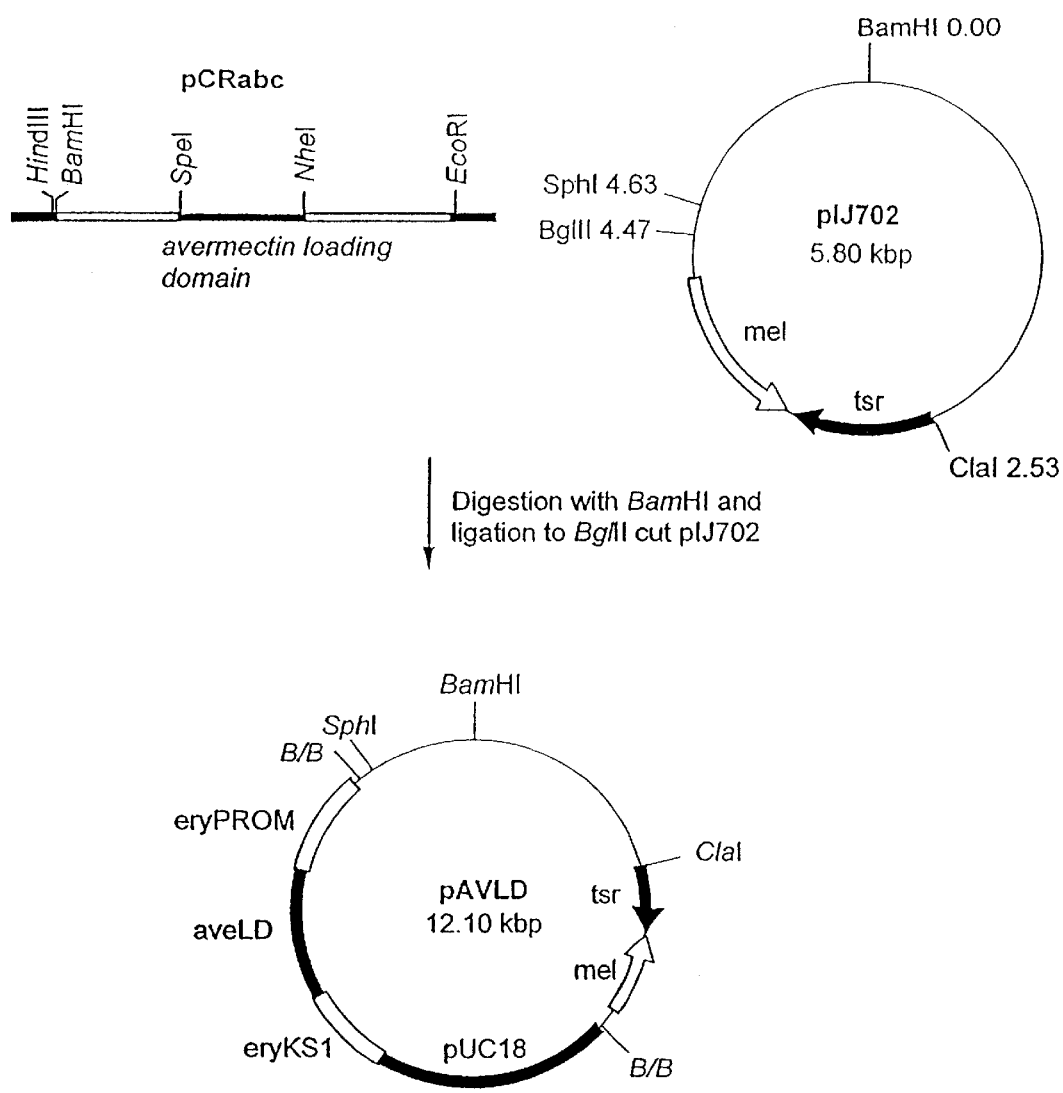
FIG. 5 is a diagram showing the construction of plasmid pAVLD.

Plasmid pCRabc (Example 1) was linearised with BamHI and ligated to plJ702 previously digested with BglII. The mixture contained the desired plasmid pAVLD (FIG. 5) The ligation mixture was transformed into E. coli TG1 recO and individual colonies were checked for their plasmid content. The desired plasmid pAVLD was identified by its restriction pattern (FIG. 5).

(ii) Construction of S. erythrea ERMD1

Figure 6:
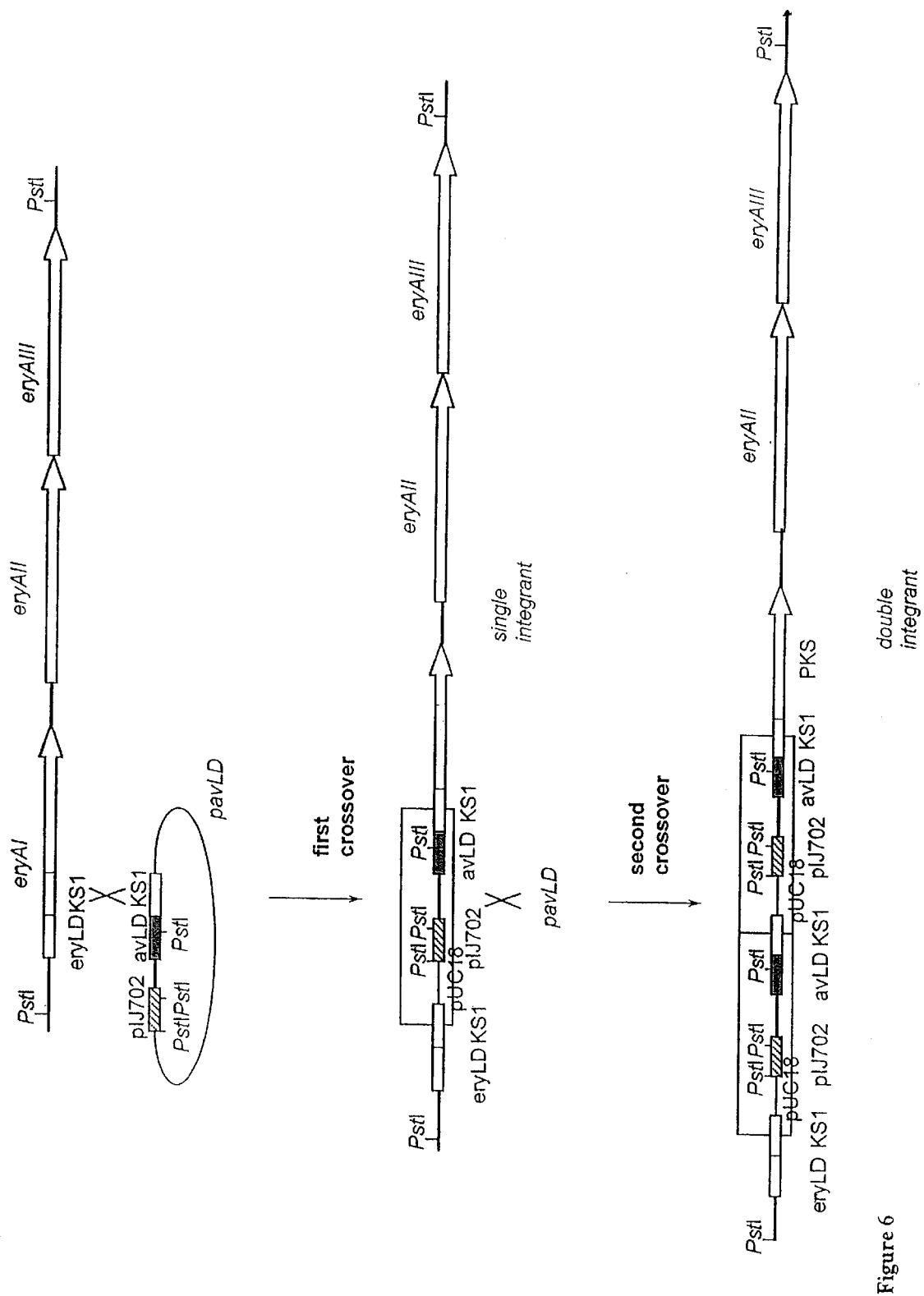
FIG. 6 shows the integration of pAVLD into the genome of S. erythraea NRRL2338.
Figure 7:
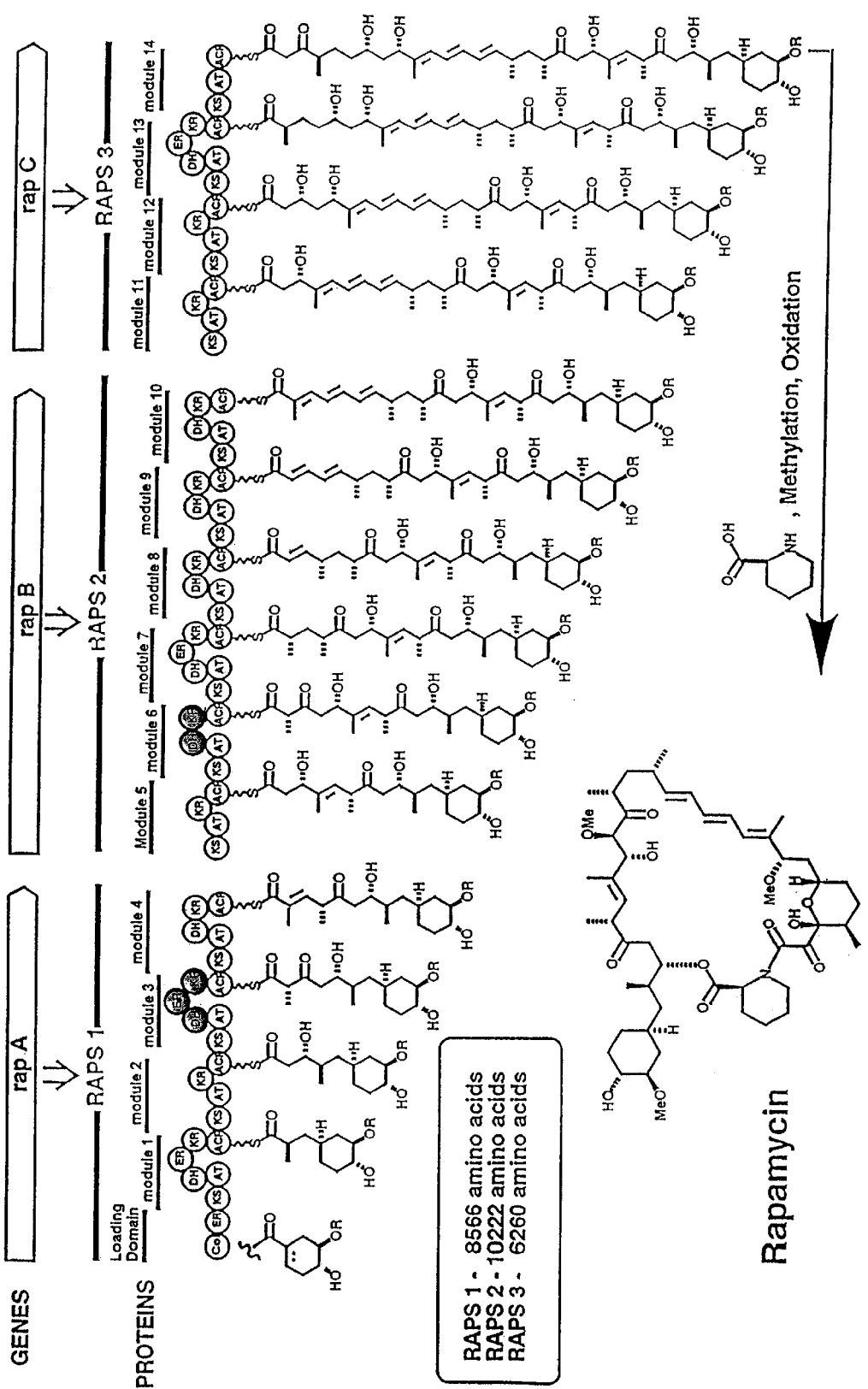
FIG. 7 is a diagram showing the biosynthesis of rapamycin.

Approximately 5–10 µg of pAVLD, isolated from E. coli TG1recO(pAVLD) was transformed into S. erythraea NRRL2338 and stable thiostrepton resistant colonies were isolated. One of these colonies was selected and total DNA was digested with PstI and analysed by Southern hybridisation employing as a probe the insert from plasmid pCRc which contains the fragment of the eryAI gene encoding the ketosynthase domain KS1. The analysis showed positively-hybridizing PstI fragments of 8.5 kbp, 4.8 kbp and 33 kbp, indicating the presence of two tandemly integrated copies of pAVLD (FIG. 6).

EXAMPLE 3

Preparation of Isopropyl and sec-Butyl Erythromycin Using S. erythraea ERMD1

A 50 mL fermentation of S. erythraea ERMD1 was carried out on tap water medium and after 4 days at 30° C. the mycelium was harvested and used to inoculate 1.5 L of sucrose-succinate medium containing thiostrepton (50 µg/mL). After growth at 30° C. for 4 days, the whole broth was extracted twice with an equal volume of ethyl acetate.

The combined extracts were concentrated under reduced pressure and subjected twice to preparative thin layer chromatography on silica plates (20×20 cm) eluted with chloroform/methanol/0.88 ammonia 8:2:0.01 (by vol). The products were further separated by HPLC on a PhaseSep C18 base-deactivated reversed-phase column S5 ODS (octadecylsilane) 6 (4.6mm×25 cm), eluted with methanol/ 0.5% ammonium acetate (70:30 (vol/vol)), at 1 mL/min. Fractions were collected between 7 and 11 minutes from three separate injections, and the pooled fractions were re-injected in ten separate injections. The analogues containing an isopropyl side chain (isopropyl at $R_1$ of formula 1) derived from the incorporation of a 4-carbon (C-4; isobutyryl) starter unit eluted earlier, with the analogues containing a sec-butyl side chain (sec-butyl at $R_1$ of formula 1) derived from the incorporation of a 5-carbon (C-5; 2-methybutyryl) starter unit emerging several minutes later. High resolution MS gave results for C-4 eryA, eryB and eryD analogues, and for C-5 eryA and eryB analogues, which correspond closely to those calculated:

| Analogue | Calc'd Mass | Measured Mass |
|---|---|---|
| C5-eryA | 762.5004 | 762.5021 |
| C4-eryA | 748.4847 | 748.4820 |
| C5-eryB | 746.4898 | 748.5077 |
| C4-eryB | 732.4898 | 732.4933 |

In these experiments natural erythromycins were present only in low or undetectable amounts, and there were no detectable amounts of eryC analogues. The overall concentration ratio of C-4/C-5 compounds in the fermentation broth, as assessed by ESMS of ethyl acetate extracts of broths, was between 4:1 and 6:1 in favour of C-4 compounds. The ratio of A:B:D analogues is variable, about 15:60:25, but with an increasing proportion of A analogues as the fermentation proceeds. The total yield of erythromycins is about 400 µg/liter. No supplementation with either isobutyric or 2-methylbutyric acid was performed. Thus, it would appear that the isobutyryl and 2-methylbutyryl starter units are derived from endogenously supplied precursors, analogous to the synthesis of natural avermectins (e.g., Hafner et al. (1991), J. Antibiot., 44:349–356).

EXAMPLE 4a

Construction of S. erythraea NRRL 2338/pIG1

Approximately 5 µg of plasmid pIG1 was transformed into protoplasts of S. erythraea NRRL 2338 and stable thiostrepton resistant colonies are isolated. From several such colonies, total DNA was obtained and analysed by Southern hybridisation, to confirm that the plasmid had integrated specifically into eryAI, and Southern analysis also showed that the site of integration was appropriate to generate a mutant capable of producing altered macrolides via the ave loading module.

EXAMPLE 4b

Construction of S. erythraea NRRL 2338/pND30

Approximately 5 µg of plasmid pND30 was transformed into protoplasts of S. erythraea NRRL 2338 and stable thiostrepton resistant colonies are isolated. From several such colonies, total DNA was obtained and analysed by Southern hybridisation, to confirm that the plasmid had integrated specifically into eryAI, and Southern analysis also showed that the site of integration was appropriate to generate a mutant capable of producing altered macrolides via the ave loading module.

EXAMPLE 5a

Preparation of 13-Isopropyl and 13-sec-Butyl Erythromycins Using S. erythraea NRRL 2338/pIG1

S. erythraea NRRL 2338/pIG1 was inoculated into tap water medium containing 50 µg/mL thiostrepton and allowed to grow for four days at 30° C. After this, 20 mL of the mycelium was used to seed 500 mL of sucrose-succinate medium containing 50 µg/mL thiostrepton, in a 2L flask with a single spring to reduce clumping, shaken at 280 rpm. After between 3.5 and 6 days, the broth was filtered to remove mycelia and then extracted three times with a quarter volume of ethyl acetate. The combined ethyl acetate extracts were dried over anhydrous sodium sulphate and solvent removed by evaporation. Analysis of the product mixture using GC and electrospray MS revealed that of a total of 5–6 mg/L of 14-membered macrolide products, the major component was sec-butyl-erythromycin D (about 1.5 mg/L), with other components present being sec-butyl-erythromycin B and sec-butyl-erythromycin A; isopropyl-erythromycins A, B and D; and small amounts of natural erythromycins A, B and D. S. erythraea NRRL 2338/pIG1 produced approximately 10–15 times more of the novel isopropyl- and sec-butyl-erythromycins compared to the equivalent S. erythraea ERMD1 construct (see Example 2) clearly demonstrating the capability of the actI promoter and its cognate activator gene actII-orf4 to enhance the expression of Type I PKS's. Again, no supplementation with either isobutyric or 2-methylbutyric acid was performed. Thus, it would appear that the isobutyryl and 2-methylbutyryl starter units are derived from endogenously supplied precursors.

EXAMPLE 5b

Preparation of 13-Isopropyl and 13-sec-Butyl Erythromycins Using S. erythraea NRRL 2338/pND30

S. erythraea NRRL 2338/pND30 was inoculated into tap water medium containing 50 µg/mL thiostrepton and allowed to grow for four days at 30° C. After this, 20 mL of the mycelium was used to seed 500 mL of sucrose-succinate medium containing 50 µg/mL thiostrepton, in a 2L flask with a single spring to reduce clumping, shaken at 280 rpm. After between 3.5 and 6 days, the broth was filtered to remove mycelia and then extracted three times with a quarter volume of ethyl acetate. The combined ethyl acetate extracts were dried over anhydrous sodium sulphate and solvent removed by evaporation. Analysis of the product mixture using GC and electrospray MS revealed that of a total of 5–6 mg/L of 14-membered macrolide products, the major component was sec-butyl-erythromycin D (about 1.5 mg/L), with other components present being sec-butyl-erythromycin B and sec-butyl-erythromycin A; isopropyl-erythromycins A, B and D; and small amounts of natural erythromycins A, B and D. S. erythraea NRRL 2338/pND30 produced approximately 10–15 times more of the novel isopropyl- and sec-butyl-erythromycins compared to the equivalent S. erythraea ERMD1 construct (see Example 2) clearly demonstrating the capability of the actI promoter and its cognate activator gene actII-orf4 to enhance the expression of Type I PKS's. Again, no supplementation with either isobutyric or 2-methylbutyric acid was performed. Thus, it would appear that the isobutyryl and 2-methylbutyryl starter units are derived from endogenously supplied precursors.

EXAMPLE 6a

Preparation of 13-cyclopentyl-erythromycin B using S. erythraea NRRL 2338/pIG1

The culture S. erythraea NRRL 2338/pIG1 was inoculated into 50 mL tap water medium in a 300 mL Erlenmeyer flask. After 36 hours incubation at 28° C., this flask was used to inoculate 3.5 L of ERY-P medium in a 5 L minijar. The broth was incubated at 28° C. with an aeration rate of 1.75 L/min. Cyclopentane carboxylic acid (1.4 mL) was added after 24 hours and the fermentation was continued for 168 hours. After this time, the whole broth was adjusted to pH 8.5 with aqueous sodium hydroxide and extracted with ethyl acetate (10 L). The ethyl acetate extract was concentrated to dryness giving the crude product as a gum (4.2 g). One gram of this extract was dissolved in ethyl acetate (5 mL) and added to a prepacked silica gel cartridge (10 g; International Sorbent Technology) previously conditioned with ethyl acetate (10 mL). The column was sequentially eluted with ethyl acetate (4×10 mL); dichloromethane:methanol (1:1) (2×10 mL); dichloromethane:methanol:ammonia (90:9:1) (1×10 mL); dichloromethane:methanol:ammonia (80:19:1) (1×10 mL); methanol (2×10 mL). Fractions 7–10 were combined and evaporated to dryness. This fractionation was repeated on the remaining 3.2 g of gum. This enrichment step yielded ca. 920 mg of a gummy solid containing the desired product. This was further purified by preparative reversed-phase HPLC using a Zorbax 7 µm ODS column (21.2 mm×25 cm) using a mobile phase of acetonitrile:0.05 M ammonium acetate (7:3) at 8 mL/min. Fractions, containing the product of interest, from four separate injections were combined and evaporated to dryness before repeat preparative reversed-phase HPLC using a Beckman 5 µm Ultrasphere ODS column (10 mm×25 cm) using a mobile phase gradient of acetonitrile:0.05 M ammonium acetate (28:72) to acetonitrile:0.05 M ammonium acetate (50:50) over 18 minutes (flow rate 4 mL/min). Fractions, containing the product of interest, from five separate injections were combined and evaporated to dryness to give a pure white solid (7 mg). The structure of the product was confirmed by mass spectrometry (MS) and nuclear magnetic resonance (NMR) spectroscopy as follows:

HPLC retention time—Method A—26.0 minutes

APCI-MS-(M+H)$^+$ observed at m/e 758, required for $C_{40}H_{72}NO_{12}$—758

33

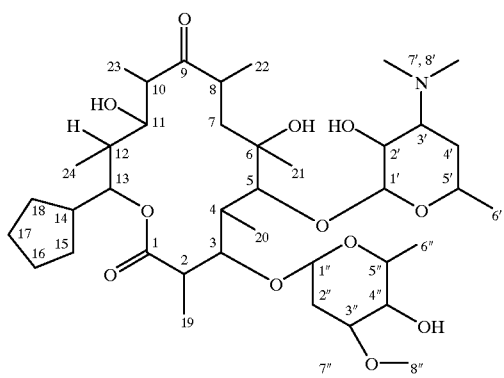

NMR data:

| Atom number | $^{13}$C chemical shift, from $^{13}$C NMR spectrum | $^1$H chemical shift and multiplicity |
|---|---|---|
| 1 | 176.0 | |
| 2 | 45.0 | 2.89 1H dq J = 9.4, 7.1 |
| 3 | 80.4 | 4.02 1H dd J = 9.4, 1.7 |
| 4 | 39.2 | 2.08 1H multiplet |
| 5 | 83.8 | 3.59 1H d J = 7.4 |
| 6 | 75.4 | — |
| 7 | 38.0 | 2.00 1H dd J = 14.7, 10.8 |
|  |  | ca. 1.65 1H multiplet |
| 8 | 45.0 | 2.71 1H dqd J = 10.6, 6.8, 2.6 |
| 9 | ca. 220.0 | — |
| 10 | 38.9* | 2.98 1H qd J = 6.8, 1.5 |
| 11 | 69.4 | 3.73 1H dd J = 9.9, 1.2 |
| 12 | 38.8* | 1.71 1H multiplet |
| 13 | 78.3 | 5.19 1H dd J = 10.5, 1.0 |
| 14 | 41.7 | 2.15 1H br sextet |
| 15 | 30.4 | ca. 1.69 1H multiplet |
|  |  | ca. 1.21 1H multiplet |
| 16 | 25.4 | ca. 1.63 1H multiplet |
|  |  | ca. 1.52 1H multiplet |
| 17 | 25.1 | ca. 1.63 1H multiplet |
|  |  | ca. 1.52 1H multiplet |
| 18 | 29.0 | ca. 1.69 1H multiplet |
|  |  | ca. 1.21 1H multiplet |
| 19 | 15.8 | 1.18 3H d J = 7.1 |
| 20 | 9.24 | 1.13 3H d J = 7.0 |
| 21 | 27.4 | 1.46 3H s |
| 22 | 18.5 | 1.14 3H d J = 6.8 |
| 23 | 9.5 | 0.99 3H d J = 6.8 |
| 24 | 9.16 | 0.86 3H d J = 7.1 |
| 1' | 103.2 | 4.43 1H d J = 7.3 |
| 2' | 70.9 | 3.24 1H dd J = 10.3, 7.3 |
| 3' | 65.4 | 2.51 1H ddd J = 12.0, 10.6, 4.1 |
| 4' | 29.0 | ca. 1.68 1H multiplet |
|  |  | ca. 1.24 1H multiplet |
| 5' | 68.8 | 3.50 1H br sextet |
| 6' | 21.5 | 1.223 1H d J = 6.1 |
| 7',8' | 40.1 | 2.32 2 × 3H s |
| 1" | 96.5 | 4.90 1H d J = 4.6 |
| 2" | 35.1 | 2.36 1H d J = 15.2 + small (<1 Hz) |
|  |  | 1.58 1H multiplet |
| 3" | 72.6 | — |
| 4" | 78.0 | 3.02 1H d J = 9.1 |
| 5" | 65.6 | 4.01 1H multiplet |
| 6" | 18.7 | 1.29 3H d J = 6.3 |
| 7" | 21.4 | 1.24 3H s |
| 8" | 49.5 | 3.31 3H s |

*Assignments for signal with asterisks may be interchangeable

34

EXAMPLE 6b

Preparation of 13-cyclopentyl-erythromycin B using S. erythraea NRRL 2338/pND30

An experiment similar to example 6a, using the culture S. erythraea NRRL 2338/pND30, produces the compound exemplified in example 6a.

EXAMPLE 7a

Preparation of 13-cyclobutyl-erythromycin B using S. erythraea NRRL 2338/pIG1

The culture S. erythraea NRRL 2338/pIG1 was inoculated into 50 mL tap water medium in 3×300 mL Erlenmeyer flasks. After 72 hours incubation at 28° C., this flask was used to inoculate 3.5 L of ERY-P medium in 3×5 L minijars. The broth was incubated at 28° C. with an aeration rate of 2.0 L/min and stirring at 500 rpm. Two feeds of cyclobutane carboxylic acid (1.4 mL) were added after 24 hours and 48 hours and the fermentation was continued for 168 hours. After this time, the pH of the whole broth was adjusted to 8.5 with aqueous sodium hydroxide and then extracted with ethyl acetate (20 L). The ethyl acetate extract was concentrated to dryness giving the crude product as a gum (9.2 g). A portion (2.3 g) of this extract was dissolved in ethyl acetate (12.5 mL) and added to a prepacked silica gel cartridge (10 g; International Sorbent Technology) previously conditioned with ethyl acetate (10 mL). The column was sequentially eluted with ethyl acetate (4×24 mL); dichloromethane:methanol (9:1) (1×24 mL); dichloromethane:methanol (8:2) (2×24 mL); dichloromethane:methanol:ammonia (80:19:1 ) (1×24 mL); methanol (1×24 mL). Fractions 6–8 were combined and evaporated to dryness. This fractionation was repeated on a remaining sample of gum (4.7 g). This enrichment step yielded ca. 415 mg of a solid containing the desired product. This was further purified by preparative reversed-phase HPLC using a Zorbax 7 μm ODS column (21.2 mm×25 cm) using a mobile phase of acetonitrile:0.05 M ammonium acetate (3:1) at 8 mL/min. Fractions, containing the product of interest, from five separate injections were combined and evaporated to dryness before repeat preparative reversed-phase HPLC using a Beckman 5 μm Ultrasphere ODS column (10 mm×25 cm) using a mobile phase gradient of acetonitrile:0.05 M ammonium acetate (28:72) to acetonitrile:0.05 M ammonium acetate (50:50) over 18 minutes (flow rate 4 mL/min). Fractions, containing the product of interest, were combined and evaporated to dryness to give a pure white solid (27 mg). The structure of the product was confirmed by MS and NMR as follows:

HPLC retention time—Method A—22.3 minutes

APCI-MS-(M+H)$^+$ observed at m/e 744, required for $C_{39}H_{70}NO_{12}$–744

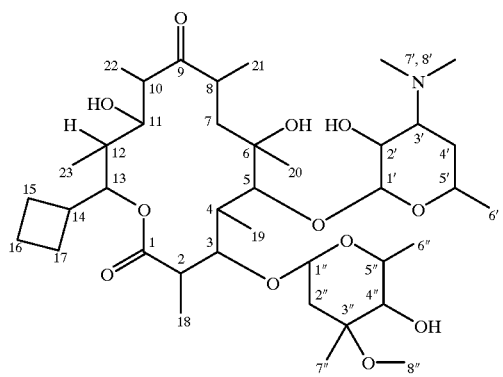

NMR data:

| Atom number | $^{13}$C chemical shift, from $^{13}$C NMR spectrum | $^1$H chemical shift and multiplicity |
| --- | --- | --- |
| 1 | 176.3 | — |
| 2 | 44.5 | 2.87 1H dq J = 91, 7.1 |
| 3 | 80.4 | 4.03 1H d J = 9.1 |
| 4 | 39.2 | 2.08 1H multiplet |
| 5 | 83.9 | 3.59 1H d J = 7.4 |
| 6 | 75.4 | — |
| 7 | 37.7 | 1.99 1H multiplet |
|   |   | 1.64 1H dd J = 15.0, 3.0 |
| 8 | 44.5 | 2.73 1H br doublet of pentets J = ca. 7.0, 3.0 |
| 9 | 219.4 | — |
| 10 | 38.9 | 2.97 1H qd J = 6.9, 1.1 |
| 11 | 69.1 | 3.75 1H dd J = 10.2 + small |
| 12 | 37.3 | 1.62 1H multiplet |
| 13 | 77.4 | 5.39 1H dd J = 9.3, 1.1 |
| 14 | 37.0 | 2.60 1H br sextet |
| 15 | 25.2 | ca 1.97 1H multiplet |
|   |   | ca 1.82 1H multiplet |
| 16 | 17.7 | ca 1.83 2H multiplet |
| 17 | 24.2 | ca 1.93 1H multiplet |
|   |   | ca 1.75 1H multiplet |
| 18 | 15.5 | 1.17 3H d J = 7.1 |
| 19 | 9.3 | 1.12 3H d J = 7.5 |
| 20 | 27.0 | 1.46 3H s |
| 21 | 18.0 | 1.14 3H d J = 7.1 |
| 22 | 9.1 | 0.98 3H d J = 6.9 |
| 23 | 9.3 | 0.81 3H d J = 7.1 |
| 1' | 103.4 | 4.43 1H d J = 7.3 |
| 2' | 70.9 | 3.27 1H dd 1 = 10.3, 7.3 |
| 3' | 65.2 | 2.64 1H multiplet |
| 4' | 29.1 | ca 1.72 1 H multiplet |
|   |   | ca 1.22 1 H multiplet |
| 5' | 68.7 | 3.52 1H br sextet J = ca. 6.1 |
| 6' | 21.0 | 1.23 3H d J = 6.1 |
| 7',8' | 40.0 | 2.38 2 × 3H s |
| 1" | 96.8 | 4.89 1H d J = 4.5 |
| 2" | 34.7 | 2.38 1H multiplet |
|   |   | 1.57 1H dd J = 15.0, 5.0 |
| 3' | 72.5 | — |
| 4" | 77.8 | 3.02 1H d J = 9.2 |
| 5" | 65.3 | 4.02 1H multiplet |
| 6" | 18.2 | 1.29 3H d J = 6.2 |
| 7" | 21.2 | 1.24 3H s |
| 8" | 49.1 | 3.31 3H s |

EXAMPLE 7b

Preparation of 13-cyclobutyl-erythromycin B using S. erythraea NRRL 2338/pND30

An experiment similar to example 7a, using the culture S. erythraea NRRL 2338/pND30, produces the compound exemplified in example 7a.

EXAMPLE 8a

Preparation of 13-(3-furanyl)-erythromycin B using S. erythraea NRRL 2338/pIG1

The culture S. erythraea NRRL 2338/pIG1 was inoculated into 50 mL tap water medium in a 300 mL Erlenmeyer flask. After 72 hours incubation at 28° C., this flask was used to inoculate 3.5 L of ERY-P medium in a 5 L minijar. The broth was incubated at 28° C. with an aeration rate of 1.75 L/min. 3-Furoic acid (1.4 g in 6 mL methanol) was added filter sterilised after 24 hours and the fermentation was continued for 138 hours. After this time, the pH of the whole broth was adjusted to 8.5 with aqueous sodium hydroxide and then extracted with ethyl acetate (10 L). The ethyl acetate extract was concentrated to dryness giving the crude product as a gum (3.8 g). A portion of this extract (1.9 g) was dissolved in ethyl acetate (10 mL) and added to a prepacked silica gel cartridge (10 g; International Sorbent Technology) previously conditioned with ethyl acetate (10 mL). The column was sequentially eluted with ethyl acetate (4×24 mL); dichloromethane:methanol (9:1) (1×24 mL); dichloromethane:methanol (8:2) (2×24 mL); dichloromethane:methanol:ammonia (80:19:1) (1×36 mL); methanol (1×24 mL). Fractions 8 and 9 were combined and evaporated to dryness. This fractionation was repeated on the remaining 1.9 g of gum. This enrichment step yielded a solid containing the desired product. This was further purified by preparative reversed-phase HPLC using a Zorbax 7 μm OS column (21.2 mm×25 cm) using a mobile phase of acetonitrile:0.05 M ammonium acetate (3:1) at 8 mL/min. Fractions, containing the product of interest, from three separate injections were combined and evaporated to dryness before repeat preparative reversed-phase HPLC using a Beckman 5 μm Ultrasphere ODS column (10 mm×25 cm) using a mobile phase gradient of acetonitrile:0.05 M ammonium acetate (28:72) to acetonitrile:0.05 M ammonium acetate (50:50) over 18 minutes (flow rate 4 mL/min). Fractions, containing the product of interest, from three separate injections were combined and evaporated to dryness to give pure 13-(3-furanyl)-erythromycin B as a white solid (9 mg). The structure of the product was confirmed by mass spectrometry.

HPLC retention time—Method A—17.0 minutes

APCI-MS-(M+H)$^+$ observed at m/e 756, required for $C_{39}H_{66}NO_{13}$—756

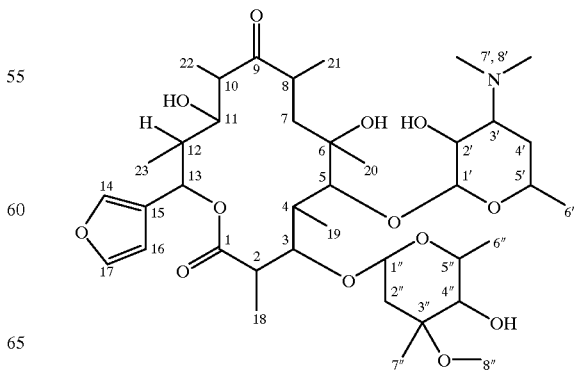

Nmr data

| Atom number | Approximate $^{13}$C chemical shift, from $^1$H—$^{13}$C correlation data | $^1$H chemical shift and multiplicity |
|---|---|---|
| 1 | 174.7 | — |
| 2 | 44.4 | 2.93 1H dq J = 8.1, 7.0 |
| 3 | 80.3 | 4.14 1H d J = 8.1 |
| 4 | 39.5 | 2.18 1H m J = 7.0, 7.2 |
| 5 | 83.9 | 3.61 1H d J = 7.2 |
| 6 | 75.0 | — |
| 7 | 37.8 | 2.07 1H dd J = 14.6, 11.3 |
|   |   | 1.70 1H dd J = 14.6, not resolved |
| 8 | 44.8 | 2.78 1H br m J = 11.3, 7.0, 2.2 |
| 9 | 219.7 | — |
| 10 | 39.2 | 3.05 1H dq J = 6.9, not resolved |
| 11 | 69.5 | 3.95 1H dd J = 10.0, not resolved |
| 12 | 41.4 | 1.88 1H dq J = 10.0, 7.0 |
| 13 | 69.2 | 6.47 1H complex m |
| 14 | 138.3 | 7.31 1H complex m J = 0.7, 1.8 |
| 15 | 124.3 | — |
| 16 | 108.6 | 6.31 1H complex m, J = 1.8, 0.7 |
| 17 | 142.8 | 7.39 1H t J = 1.8 |
| 18 | 15.5 | 1.21 3H d J = 7.0 |
| 19 | 8.7 | 1.16 3H d J = 7.0 |
| 20 | 27.0 | 1.48 3H s |
| 21 | 18.3 | 1.18 3H d J = 7.0 |
| 22 | 8.4 | 1.03 3H d J = 6.9 |
| 23 | 8.7 | 0.88 3H d J = 7.0 |
| 1' | 103.3 | 4.46 1H d J = 7.4 |
| 2' | 71.1 | 3.29 1H m |
| 3' | 65.1 | 2.60 1H broad m |
| 4' | 29.3 | 1.78 1H m |
|   |   | 1.24 1H m |
| 5' | 68.8 | 3.54 1H m |
| 6' | 20.7 | 1.24 3H d (obscured) |
| 7',8' | 40.0 | 2.39 2 × 3H s |
| 1" | 96.6 | 4.88 1H brd J = 4.9 |
| 2" | 35.2 | 2.39 1H m |
|   |   | 1.59 1H dd j = 15.0, 4.9 |
| 3" | 71.7 | — |
| 4" | 77.8 | 3.03 1 H d (obscured) |
| 5" | 66.1 | 4.03 1H dq J = 9.0, 6.1 |
| 6" | 18.3 | 1.30 3H d J = 6.1 |
| 7" | 21.2 | 1.26 3H s |
| 8" | 49.1 | 3.33 3H s |

*Assignments indicated with an asterisk may be reversed

EXAMPLE 8b

Preparation of 13-(3-furanyl)-erythromycin B using S. erythraea NRRL 2338/pND30

An experiment similar to example 8a, using the culture S. erythraea NRRL 2338/pND30, produces the compound exemplified in example 8a.

EXAMPLE 9a

Preparation of 13-cyclopropyl-erythromycin B using S. erythraea NRRL 2338/pIG1

The culture S. erythraea NRRL 2338/pIG1 was inoculated into 50 mL tap water medium in a 300 mL Erlenmeyer flask. After 72 hours incubation at 28° C., this flask was used to inoculate 3.5 L of ERY-P medium. Thiostreptone (105 mg) was added immediately after sterilisation. The broth was incubated at 28° C. with an aeration rate of 2 L/min and stirring at 500 rpm. Cyclopropane carboxylic acid (1.2 mL) was added after 24 hours and the fermentation was continued for 144 hours. After this time, the whole broth was adjusted to pH 8.5 with aqueous sodium hydroxide and then extracted with ethyl acetate (3 L). The ethyl acetate extract was concentrated to dryness giving the crude product as a gum (1.7 g). This extract (0.85 g) was dissolved in ethyl acetate (10 mL) and added to a prepacked silica gel cartridge (10 g; International Sorbent Technology) previously conditioned with ethyl acetate (20 mL). The column was sequentially eluted with ethyl acetate (4×24 ML); dichloromethane:methanol (9:1) (1×24 mL); dichloromethane:methanol (8:2) (1×24 mL); dichloromethane:methanol:ammonia (80:19:1) (3×24 mL); methanol (1×24 mL). Fractions 6–9 were combined and evaporated to dryness. This fractionation was repeated on the remaining 0.85 g of gum. This enrichment step yielded a solid containing the desired product. This was further purified by preparative reversed-phase HPLC using a Zorbax 7 μm ODS column (21.2 mm×25 cm) using a mobile phase of acetonitrile:0.05 M ammonium acetate (3:1) at 8 mL/min. Fractions, containing the product of interest, from 4 separate injections were combined and evaporated to dryness before repeat preparative reversed-phase HPLC using a Beckman 5 μm Ultrasphere ODS column (10 mm×25 cm) using a mobile phase gradient of acetonitrile:0.05 M ammonium acetate (28:72) to acetonitrile:0.05 M ammonium acetate (50:50) over 18 minutes (flow rate 4 mL/min). Fractions, containing the product of interest, from three separate injections were combined and evaporated to dryness to give pure 13-cyclopropyl-erythromycin B as a white solid (9 mg). The structure of the product was confirmed by mass spectrometry.

HPLC retention time—Method A—17.9 minutes

APCI-MS-(M+H)$^+$ observed at m/e 730, required for $C_{38}H_{68}NO_{12}$–730

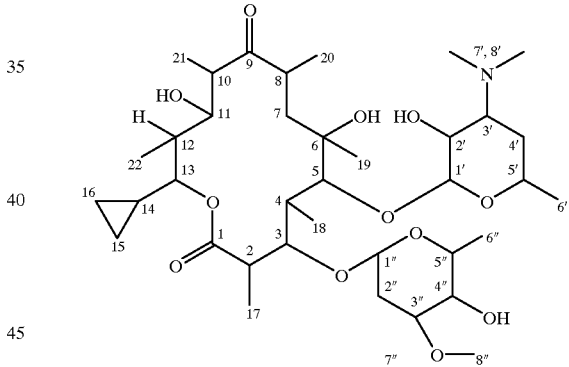

NMR data

| Atom number | Approximate $^{13}$C chemical shift, from $^1$H—$^{13}$C correlation data | $^1$H chemical shift and multiplicity |
|---|---|---|
| 1 | 176.4 | — |
| 2 | 44.8 | 2.88 1H dq J = 8.5, 7.1 |
| 3 | 80.3 | 4.04 1H dd J = 8.5, 1.9 |
| 4 | 39.5 | 2.11 1H br pentet J = ca 7 |
| 5 | 83.7 | 358 1H d J = 7.5 |
| 6 | 75.2 | — |
| 7 | 38.0 | 2.02 1H dd J = 14.7, 10.9 |
|   |   | 1.66 1H dd J = 14.7, 2.8 |
| 8 | 45.1 | 2.74 1H dqd J = 10.9, 7.1, 2.8 |
| 9 | 220.0 | — |
| 10 | 39.0 | 3.01 1H multiplet |
| 11 | 69.8 | 3.76 1H dd J = 10.0, ca 1.4 |
| 12 | 40.4 | 1.84 1H dqd J = 10.0, 6.9, 1.2 |
| 13 | 78.5 | 4.68 1H dd J = 9.2, 1.2 |

-continued

| Atom number | Approximate $^{13}$C chemical shift, from $^1$H—$^{13}$C correlation data | $^1$H chemical shift and multiplicity |
|---|---|---|
| 14 | 13.2 | 1.09 1H multiplet |
| 15 | 4.1 | 0.51 1H multiplet |
|  |  | 0.42 1H multiplet |
| 16 | 2.7 | 0.51 1H multipfet |
|  |  | 0.29 1H multiplet |
| 17 | 15.1 | 1.19 3H d J = 7.1 |
| 18 | 9.3 | 1.14 3H d J = ca 7.1 |
| 19 | 27.4 | 1.46 3H s |
| 20 | 18.3 | 1.16 3H d J = 7.1 |
| 21 | 9.3 | 1.001 3H d J = ca 7.2* |
| 22 | 9.3 | 0.998 3H d J = ca 6.9* |
| 1' | 103.3 | 4.43 1H d J = 7.2 |
| 2' | 71.0 | 3.25 1H dd J = 10.3, 7.2 |
| 3' | 65.6 | 2.54 1H br ddd J = ca 12.5, 10.3, 4 |
| 4' | 29.0 | 1.69 1H multiplet |
|  |  | 1.25 1H multiplet |
| 5' | 69.2 | 3.51 1H br dq J = ca 11, 6 |
| 6' | 20.9 | 1.22 3H d J = 6.2 |
| 7',8' | 39.9 | 2.33 2 × 3H s |
| 1" | 97.1 | 4.87 1H brd J = ca5 |
| 2" | 35.0 | 2.37 1H brd J = ca. 15 |
|  |  | 1.57 1H dd J = 15.1, 5.0 |
| 3" | 72.5 | — |
| 4" | 78.1 | 3.01 1H brd J = 9.2 |
| 5" | 66.0 | 4.02 1H dq J = 9.2, 6.2 |
| 6" | 18.3 | 1.28 3H d J = ca 6.2 |
| 7" | 21.0 | 1.24 3H s |
| 8" | 49.3 | 3.32 3H s |

*Assignments indicated with an asterisk maybe reversed

EXAMPLE 9b

Preparation of 13-cyclopropyl-erythromycin B using *S. erythraea* NRRL 2338/pND30

An experiment similar to example 9a, using the culture *S. erythraea* NRRL 2338/pND30, produces the compound exemplified in example 9a.

EXAMPLE 10a

Preparation of 13-(1-methylthio-ethyl)-erythromycin B using *S. erythraea* NRRL 2338/pIG1

The culture *S. erythraea* NRRL 2338/pIG1 was inoculated into 1 L tap water medium in a 2.8 L Fernbach flask. Thiostreptone (50 mg) was added immediately after inoculation. After 84 hours incubation at 29° C., this flask was used to inoculate 8 L of supplemented ERY-P medium (50 g/L Dextrose, 30 g/L Nutrisoy flour, 3 g/L ammonium sulfate, 5 g/L NaCl, 6 g/L CaCO$_3$, 10 g/L sucrose, 5 g/L corn steep solids, 0.5 g/L MGSO$_4$ and 1 mL/L of P2000) in a 14 L fermentor jar. The broth was incubated at 28° C. with an aeration rate of 8 L/min, stirring at 800 rpm and with pH maintained between 6.9 and 7.3 with NaOH or H$_2$SO$_4$ (15%). Methylthiolactic acid (3.2 mL) was added after 24 and 48 hours. Additional methylthiolactic acid (1.6 mL) was added after 120 hours. The fermentation was continued for 142 hours. After this time, the whole broth was centrifuged to yield centrate (34 L) which was loaded onto a XAD-16 resin column (600 mL; Rohm and Haas). The resin column was then washed with water (1.8 L) and eluted with ethyl acetate (2.5 L). The ethyl acetate was partially concentrated (to 250 mL) and then the product of interest was extracted into 100 mM sodium phosphate buffer, pH 3.5 (1.3 L). The product was transferred back into ethyl acetate by adjusting the water to pH 9 with sodium hydroxide and then mixing with ethyl acetate (450 mL). The erythromycin rich ethyl acetate layer was separated, evaporated to a gum (5.0 g), and then resuspended into 20% methanol (120 mL) which was loaded onto a CG-161 resin column (100 mL; Toso Haas). The resin column was sequentially eluted with 20% methanol (3×100 mL), 40% methanol (3×100 mL), 60% methanol (3×100 mL), 80% methanol (3×100 mL) and neat methanol (4×100 mL). The neat methanol fractions 2 and 3, containing the product of interest, were evaporated to a solid (220 mg) and further purified over a reversed-phase 10 $\mu$m Kromasil C18 HPLC column (75 mm×25 cm), using a mobile phase of acetonitrile:0.05 M ammonium acetate with 0.1% trifluoroacetic acid gradient (32:68) to (38:62) over 60 minutes at a flow rate of 215 mL/min. Fractions containing the product of interest were combined (1.7 L), adjusted to pH 9 with sodium hydroxide and extracted into methylene chloride (300 mL). The methylene chloride layer was separated and evaporated to dryness to yield partially pure product. The preparative HPLC step and extraction step was repeated to obtain pure 13-(1-methylthio-ethyl)-erythromycin B (31 mg). The structure of the product was confirmed by MS and NMR spectroscopy (Bruker DMX 500 MHz spectrometer) as follows:

HPLC retention time—Method B—14.9 minutes

APCI-MS-(M+H)$^+$ observed at m/e 764, required for C$_{38}$H$_{70}$NO$_{12}$S-764

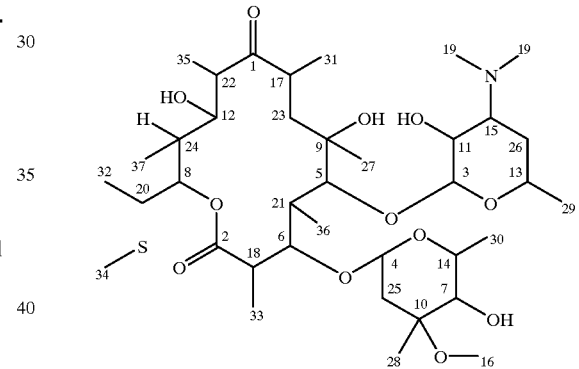

NMR data:

| Atom # | $^{13}$C(ppm) | # Attached $^1$H | $^1$H (ppm) |
|---|---|---|---|
| 1 | 221.08 | 0 |  |
| 2 | 176.10 | 0 |  |
| 3 | 103.42 | 1 | 4.49 |
| 4 | 96.93 | 1 | 4.94 |
| 5 | 84.31 | 1 | 3.63 |
| 6 | 80.69 | 1 | 4.06 |
| 7 | 78.30 | 1 | 3.07 |
| 8 | 76.17 | 1 | 5.42 |
| 9 | 75.75 | 0 |  |
| 10 | 73.11 | 0 |  |
| 11 | 71.23 | 1 | 3.32 |
| 12 | 69.84 | 1 | 3.17 |
| 13 | 69.03 | 1 | 3.56 |
| 14 | 66.18 | 1 | 4.06 |
| 15 | 65.99 | 1 | 2.68 |
| 16 | 49.91 | 3 | 3.36 |
| 17 | 45.62 | 1 | 2.74 |
| 18 | 45.26 | 1 | 2.96 |
| 19 | 40.61 | 3 | 2.46 |
| 20 | 40.01 | 1 | 2.83 |
| 21 | 39.60 | 1 | 2.14 |

-continued

| Atom # | $^{13}$C(ppm) | # Attached $^1$H | $^1$H (ppm) |
|---|---|---|---|
| 22 | 38.94 | 1 | 3.04 |
| 23 | 38.44 | 2 | 2.03/1.70 |
| 24 | 37.68 | 1 | 2.44 |
| 25 | 35.47 | 2 | 2.41/1.63 |
| 26 | 29.66 | 2 | 1.79/1.32 |
| 27 | 27.70 | 3 | 1.51 |
| 28 | 21.89 | 3 | 1.29 |
| 29 | 21.77 | 3 | 1.28 |
| 30 | 19.08 | 3 | 1.33 |
| 31 | 18.92 | 3 | 1.20 |
| 32 | 18.19 | 3 | 1.33 |
| 33 | 16.29 | 3 | 1.23 |
| 34 | 11.11 | 3 | 2.12 |
| 35 | 10.16 | 3 | 1.07 |
| 36 | 9.70 | 3 | 1.17 |
| 37 | 9.62 | 3 | 0.90 |

EXAMPLE 10b

Preparation of 13-(1-methylthio-ethyl)-erythromycin B using S. erythraea NRRL 2338/pND30

An experiment similar to example 10a, using the culture S. erythraea NRRL 2338/pND30, produces the compound exemplified in example 10a.

EXAMPLE 11

Preparation of 13-cyclobutyl-erythromycin B using S. erythraea NRRL 2338

The culture S. erythraea NRRL 2338 was inoculated into 50 mL tap water medium in a 300 mL Erlenmeyer flask. After 48 hours incubation at 28° C., this flask was used to inoculate 50 mL of ERY-P medium in a 300 mL Erlenmeyer flask. The broth was incubated at 28° C. Cyclobutane carboxylic acid (20 mL) was added after 24 hours and the fermentation was continued for 168 hours. After this time, the whole broth was adjusted to pH 8.5 with aqueous sodium hydroxide and then extracted with ethyl acetate (50 mL). The ethyl acetate was separated and concentrated to dryness. The sample was redissolved in methanol (1 mL) for HPLC-MS analysis. This confirmed the production of 13-cyclobutyl-erythromycin B, by the untransformed, non-recombinant NRRL 2338 as described in example 7 for the genetically-engineered strain containing the avr loading module (NRRL 2338/pIG1 construct).

HPLC retention time—Method A—22.3 minutes

APCI-MS-(M+H)$^+$ observed at m/e 744, required for $C_{39}H_{70}NO_{12}$–744

EXAMPLE 12

Preparation of 13-cyclopropyl-erythromycin B using S. erythraea NRRL 2338

The culture S. erythraea NRRL 2338 was inoculated into 50 mL tap water medium in a 300 mL Erlenmeyer flask. After 48 hours incubation at 28° C., this flask was used to inoculate 50 mL of ERY-P medium in a 300 mL Erlenmeyer flask. The broth was incubated at 28° C. Cyclopropane carboxylic acid (20 mL) was added after 24 hours and the fermentation was continued for 168 hours. After this time, the whole broth was adjusted to pH 8.5 with aqueous sodium hydroxide and then extracted with ethyl acetate (50 mL). The ethyl acetate was separated and concentrated to dryness. The sample was redissolved in methanol (1 mL) for HPLC-MS analysis.

This confirmed the production of 13-cyclopropyl-erythromycin B, by the untransformed, non-recombinant NRRL 2338 as described in example 9 for the genetically-engineered strain containing the avr loading module (NRRL 2338/pIG1 construct).

HPLC retention time—Method A—17.9 minutes

APCI-MS-(M+H)$^+$ observed at m/e 730, required for $C_{38}H_{68}NO_{12}$–730

EXAMPLE 13a

Preparation of 13-cyclobutyl-erythromycin A using S. erythraea NRRL 2338/pIG1

The culture S. erythraea NRRL 2338/pIG1 was inoculated into 50 mL tap water medium in 3×300 mL Erlenmeyer flasks. After 72 hours incubation at 28° C., each flask was used to inoculate 3.5 L of ERY-P medium in 3×5 L minijars. The broth was incubated at 28° C. with an aeration rate of 2.0 L/min and stirring at 500 rpm. Two feeds of cyclobutane carboxylic acid (1.4 mL) were added after 24 hours and 48 hours and the fermentation was continued for 168 hours. After this time, the pH of the whole broth was adjusted to 8.5 with aqueous sodium hydroxide and then extracted with ethyl acetate (20 L). The ethyl extract was concentrated to dryness giving the crude product as a gum (9.2 g). A portion (2.3 g) of this extract (2.3 g) was dissolved in ethyl acetate (12.5 mL) and added to a prepacked silica gel cartridge (10 g; International Sorbent Technology) previously conditioned with ethyl acetate (10 mL). The column was sequentially eluted with ethyl acetate (4×24 mL); dichloromethane:methanol (9:1) (1×24 mL); dichloromethane:methanol (8:2) (2×24 mL); dichloromethane:methanol:ammonia (80:19:1) (1×24 mL); methanol (1 ×24 mL). Fractions 6–8 were combined and evaporated to dryness. This fractionation was repeated on the remaining 4.7 g of gum. This enrichment step yielded 415 mg of a solid containing the desired product. This was further purified by preparative reversed-phase HPLC using a Zorbax 7 µm ODS column (21.2 mm×25 cm) using a mobile phase of acetonitrile:0.05 M ammonium acetate (3:1) at 8 mL/min. Fractions, containing the product of interest, from 5 separate injections were combined and evaporated to dryness before repeat preparative reversed-phase HPLC using a Beckman 5 µm Ultrasphere ODS column (10 mm×25 cm) using a mobile phase gradient of acetonitrile:0.05 M ammonium acetate (28.72) to acetonitrile:0.05 M ammonium acetate (50:50) over 18 minutes (flow rate 4 mL/min) Fractions, containing the product of interest, were combined and evaporated to dryness to give a pure white solid (4 mg). The structure of the product was confirmed by MS and NMR spectroscopy as follows:

HPLC retention time—Method A—17.5 minutes

APCI-MS-(M+H)$^+$ observed at m/e 760, required for $C_{39}H_{70}NO_{13}$–760

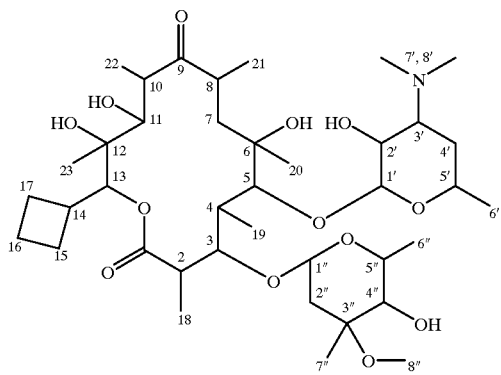

Nmr data:

| Atom number | Approximate $^{13}C$ chemical shift, from $^1H$—$^{13}C$ correlation data | $^1H$ chemical shift and multiplicity |
|---|---|---|
| 1 | 176.1 | — |
| 2 | 44.7 | 2.88 1H multiplet |
| 3 | 79.8 | 3.99 1H multiplet |
| 4 | 39.3 | 1.97 1H multiplet |
| 5 | 83.4 | 3.57 1H d J = 7.6 |
| 6 | 75.4 | — |
| 7 | 38.3 | 1.92 1H multiplet |
|   |   | 1.72 1H multiplet |
| 8 | 45.1 | 2.70 1H multiplet |
| 9 | 222.5 | — |
| 10 | 37.4 | 3.07 1H brq J = 7.0 |
| 11 | 69.1 | 3.77 1H brs |
| 12 | 76.1 |   |
| 13 | 77.1 | 5.10 1H d J = 7.1 |
| 14 | 34.8 | 2.86 1H multiplet |
| 15 | 26.7 | 1.98 1H multiplet |
|   |   | 1.80 1H multiplet |
| 16 | 18.8 | 1.88 1H multiplet |
|   |   | 1.71 1H multiplet |
| 17 | 24.8 | 1.89 2H multiplet |
| 18 | 15.8 | 1.19 3H d J = 7.0 |
| 20 | 26.9 | 1.47 3H s |
| 21 | 18.1 | 1.16 3Hd J = 7.0 |
| 1' | 103.0 | 4.42 1Hd J = 7.2 |
| 2' | 71.0 | 3.24 1H dq J = 10.4, 7.2 |
| 3' | 65.3 | 2.51 1H multiplet |
| 4' | 28.7 | 1.68 1H multiplet |
|   |   | 1.26 1H multiplet |
| 5' | 69.2 | 3.49 1H multiplet |
| 6' | 21.3 | 1.23 3H d J = 6.2 |
| 7',8' | 40.0 | 2.38 2 × 3H s |
| 1" | 96.3 | 4.89 1H d J = 4.5 |
| 2" | 34.7 | 2.38 1H multiplet |
|   |   | 1.57 1H dd J = 15.0, 5.0 |
| 3" | 73.0 | — |
| 4" | 78.0 | 3.02 1H d J = 9.4 |
| 5" | 65.6 | 4.00 1H multiplet |
| 6" | 18.4 | 1.29 3H d J = 6.2 |
| 7" | 21.3 | 1.24 3H s |
| 8" | 49.4 | 3.32 3H s |

EXAMPLE 13b

Preparation of 13-cyclobutyl-erythromycin A using S. erythraea NRRL 2338/pND30

An experiment similar to example 13a, using the culture S. erythraea NRRL 2338/pND30, produces the compound exemplified in example 13a.

EXAMPLE 14a

Preparation of 13-cyclopropyl-erythromycin A using S. erythraea NRRL 2338/pIG1

Six 2800 mL Fernbach flasks were inoculated with S. erythraea NRRL 2338/pIG1. Each flask contained 1 L of tap water medium with 50 mg of thiostreptone added to each flask. After 24 hours of incubation at 28° C., 200 ppm of cyclopropane carboxylic acid was added to each flask. The flasks were incubated for 90 hours and composited into a sterile, 8 L aspirator bottle. The aspirator bottle was used to inoculate 314 gallons of ERY-P medium in a 500 gallon pilot vessel. The broth was incubated, run at 27° C. to 29° C., at a pH ranging from 6.7 to 7.4, with an aeration rate of 20 standard cubic feet/min and stirring at 175 rpm. Cyclopropane carboxylic acid (200 mg/L) was added after 33 hours, 81 hours and 117 hours. The fermentation was continued for 198 hours. After this time, the whole broth was filtered over a 0.2 μm, ceramic filter (30 ft$^2$, U.S. Filter). The filtrate was loaded onto an XAD-16 resin column (12 L; Rohm and Haas). The resin column was then eluted with ethyl acetate (60 L). The ethyl acetate was concentrated to a gum (302 g) to which 2 L of methylene chloride was added. The resulting methylene chloride solution was washed with 8 L of 250 mM sodium bicarbonate buffer, pH 9. The erythromycin rich methylene chloride layer was separated, evaporated to a gum (200 g), and then resuspended into 40% methanol (10 L) which was loaded onto a CG-161 resin column (9 L; Toso Haas). The resin column was washed with 40% methanol (30 L) and sequentially eluted with 75% methanol (8×10 L) and neat methanol (3×10 L). The 75% methanol fractions 5 through 8, containing the product of interest, were combined, and evaporated to 3.2 L. The concentrate was adjusted to pH 9 and added to 0.95 L of methylene chloride. The methylene chloride layer was separated and evaporated to yield 12.4 g of a gum. Part of the gum (six grams) was further purified by preparative reversed-phase HPLC using a Kromasil 10 μm C18 HPLC column (75 mm×25 cm), using a mobile phase of methanol:0.05 M ammonium acetate with 0.1% trifluoroacetic acid isocaratic (50:50) at a flow rate of 215 mL/min. Fractions containing the product of interest were combined (230 mL), evaporated to a concentrate (110 mL), adjusted to pH 9 with sodium hydroxide, and extracted into methylene chloride (50 mL). The methylene chloride layer was separated and evaporated to dryness to yield 630 mg of partially pure product. Another portion of the gum (one gram) was further purified by preparative reversed-phase HPLC using a MetaChem Inertsil 10 μm C8 column (50 mm×25 cm) using a mobile phase of acetonitrile:0.05 M ammonium acetate with 0.1% trifluoroacetic acid gradient (20:80) to (25:75) over 50 minutes at a flow rate of 125 mL/min. Fractions, containing the compound of interest (28–46 minutes), were combined, saturated with sodium bicarbonate and extracted with methylene chloride. The methylene chloride was separated and evaporated to dryness to yield 361 mg of partially pure product. A portion of these partially pure materials was further purified by reversed-phase HPLC as exemplified by: Phenomenex Prodigy 10 μm C18 column (50×250 mm) using a mobile phase of methanol:0.05 M ammonium acetate with 0.1% trifluoroacetic acid isocratic (50:50) at a flow rate of 100 mL/min. Fractions, containing the product of interest (27–31 minutes), were combined, saturated with sodium bicarbonate, and extracted with methylene chloride. The methylene chloride was separated and evaporated to dryness to yield partially pure product. Material was further purified by preparative reversed-phase HPLC using a Phenomenex Prodigy 10 μm C18 column (50 mm×25 cm) using a mobile phase of methanol:0.05 M ammonium acetate with 0.1% trifluroacetic acid isocratic (48:52) at a flow rate of 100 mL/min. Fractions containing the product of interest (41–45 minutes) were combined, saturated with sodium bicarbonate, and extracted with methylene chloride. The methylene chloride was separated and evaporated to dryness to yield 13-cyclopropyl-erythromycin A as a solid (20 mg). The structure of the product was confirmed by MS and NMR spectroscopy Bruker DMX 500 MHz spectrometer) as follows:

HPLC retention time—Method B—5.6 minutes

APCI-MS-(M+H)$^+$ observed at m/e 746, required for $C_{38}H_{66}NO_{13}$–746

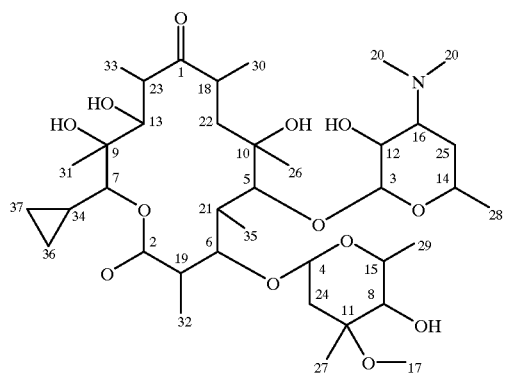

NMR data:

| Atom # | $^{13}$C (ppm) | # Attached $^1$H | $^1$H (ppm) |
|---|---|---|---|
| 1 | 222.41 | 0 | |
| 2 | 175.88 | 0 | |
| 3 | 103.63 | 1 | 4.45 |
| 4 | 96.75 | 1 | 4.92 |
| 5 | 83.92 | 1 | 3.60 |
| 6 | 80.25 | 1 | 4.02 |
| 7 | 78.52 | 1 | 4.74 |
| 8 | 78.42 | 1 | 3.05 |
| 9 | 75.99 | 0 | |
| 10 | 75.49 | 0 | |
| 11 | 73.05 | 0 | |
| 12 | 71.31 | 1 | 3.27 |
| 13 | 69.46 | 1 | 3.84 |
| 14 | 69.39 | 1 | 3.52 |
| 15 | 66.02 | 1 | 4.04 |
| 16 | 65.95 | 1 | 2.49 |
| 17 | 49.93 | 3 | 3.36 |
| 18 | 45.47 | 1 | 2.74 |
| 19 | 45.23 | 1 | 2.89 |
| 20 | 40.70 | 1 | 2.34 |
| 21 | 40.00 | 1 | 2.02 |
| 22 | 38.94 | 2 | 1.96/1.76 |
| 23 | 38.46 | 1 | 3.15 |
| 24 | 35.38 | 2 | 2.41/1.61 |
| 25 | 29.07 | 2 | 1.71/1.28 |
| 26 | 27.36 | 3 | 1.50 |
| 27 | 21.94 | 3 | 1.28 |
| 28 | 21.84 | 3 | 1.26 |
| 29 | 19.08 | 3 | 1.32 |
| 30 | 18.69 | 3 | 1.21 |
| 31 | 17.38 | 3 | 1.31 |
| 32 | 16.11 | 3 | 1.21 |
| 33 | 12.38 | 3 | 1.20 |
| 34 | 10.64 | 1 | 1.20 |
| 35 | 9.60 | 3 | 1.16 |
| 36 | 4.23 | 2 | 0.67/1.33 |
| 37 | 1.64 | 2 | 0.47/0.32 |

EXAMPLE 14b

Preparation of 13-cyclopropyl-erythromycin A using S. eythraea NRRL 2838/pND30

An experiment similar to example 14a, using the culture S. erythraea NRRL 2338/pND30, produces the compound exemplified in example 14a.

EXAMPLE 15a

Preparation of 13-(3-thienyl)-erythromycin B using S. erythraea NRRL 2338/pIG1

The culture S. erythraea NRRL 2338/pIG1 was inoculated into 50 mL tap water medium in a 300 mL Erlenmeyer flask. After 48 hours incubation at 28° C. 5 mL of this inoculum was used to inoculate 50 mL of ERY-P medium in a 300 mL Erlemneyer flask. The broth was incubated at 28° C. The N-acetyl cysteamine thioester of 3-thiophene carboxylic acid (20 mg in 0.5 mL of methanol) was added filter sterilised after 24 hours and the fermentation was continued for 168 hours. After this time, the whole broth was adjusted to pH 8.5 with aqueous sodium hydroxide and then extracted with ethyl acetate (50 mL). The ethyl acetate was separated and concentrated to dryness. The sample was redissolved in methanol (1 mL) for HPLC-MS analysis. This confirmed the production of 13-(3-thienyl)-erythromycin B.

HPLC retention time—Method A—20.0 minutes

APCI-MS-(M+H)$^+$ observed at m/e 772, required for $C_{39}H_{66}NO_{12}S$-772

EXAMPLE 15b

Preparation of 13-(3-thienyl)-erythromycin B using S. erythraea NRRL 2338/pND30

An experiment similar to example 15a, using the culture S. erythraea NRRL 2338/pND30, produces the compound exemplified in example 15a.

EXAMPLE 16

Preparation of 6-deoxy-13-cyclopropyl-erythromycin B using S. erythraea NRRL 18643

The culture S. erythraea NRRL 18643, an eryF mutant of S. erythraea (Science, 252:114, Apr. 5, 1991) was inoculated into 1 L tap water medium in a 2.8 L Fernbach flask. Cyclopropane carboxylic acid (200 mL) was added after 24 hours incubation at 29° C. with 200 rpm agitation. After three (3) days total incubation, one flask was used to inoculate 8 L of supplemented ERY-P medium (60 g/L cerelose, 30 g/L Nutrisoy flour, 3 g/L $(NH_4)_2SO_4$, 5 g/L NaCl, 6 g/L corn steep solids, 0.5 g/L $MgSO_4$, and 1 mL/L P2000) in 14 L fermentor jars. The broth was incubated at 28° C. with an aeration rate of 8 L/min, stirring at 800 rpm and with pH maintained between 6.9 and 7.3 with NaOH or $H_2SO_4$ (15%). Cyclopropane carboxylic acid (1.6 mL) was added after 24 and 48 hours. The fermentation, done in duplicate, was harvested after 163 hours total incubation time. The pH of the whole broth was adjusted to 9 with sodium hydroxide, and the broth was extracted with ethyl acetate (16 L). The ethyl acetate was concentrated to an oil in a 20 L Buchi rotoevaporation unit. The oil was redissolved with 500 mL of methylene chloride. Five hundred mL of water was added to this liquid, and the pH of the aqueous phase was adjusted to 9 with 10% ammonium hydroxide. After shaking vigorously, the methylene chloride layer was collected, and evaporated in a 1 L rotoevaporation flask to yield 11.0 g of oily residue. This material was dissolved with 250 mL of a 4:6 methanol:water solution, and loaded onto an 80 mL CG-161 resin column (Toso Haas). The column was washed with 350 mL of 4:6 methanol:water solution. The column was then briefly washed at 8 mL/min with a 7:3 methanol:water solution, until colored impurities began to elute from the column (approximately 2 bed volumes wash). At this time, a 1 hour gradient run was initiated, with the concentration of methanol changing from 70% to 100%, over a 1 hour period, at a flow of 8 mL/min. The fraction containing the product of interest was evaporated to dryness and further purified on a reversed-phase 10 μm Kromasil C18 HPLC column (50 mm×25 cm), using a mobile phase of acetonitrile:buffer consisting of 0.01 M ammonium acetate, 0.02% trifluoroacetic acid, and 26% acetonitrile (5:95) for 50 minutes at a flow rate of 120 mL/min. This was followed by a linear gradient from (5:95) to (33:67) over the next 40 minutes. Fractions containing the product of interest were combined (530 mL), adjusted to a pH of 9 with 10% ammonium hydroxide, and extracted into methylene chloride (400 mL). The methylene chloride layer was separated and evaporated to dryness to yield purified 6-deoxy-13-cyclopropyl-erythromycin B (12 mg). The structure of the product was confirmed by MS.

HPLC retention time—method B—21.4 minutes

APCI mass spectroscopy—(M+H)$^+$ observed at m/e 714, required for $C_{38}H_{66}NO_{12}$–714

EXAMPLE 17

Preparation of 6-deoxy-13-propyl-erythromycin B using *S. erythraea* NRRL 18643

*S. erythraea* NRRL 18643 was inoculated from a three day patch on_YPD agar (0.5% Difco yeast extract, 0.5% Difco Bacto peptone, 0.25% dextrose, 0.5% MOPS, 1.7% Difco Basto agar, pH adjusted to 7.0) into 25 mL of_YPD broth (0.5% Difco yeast extract, 0.5% Difco Bacto peptone, 0.25% dextrose, 0.5% MOPS, pH adjusted to 7.0) in a 250 mL Erlenmeyer flask. The flask was incubated at 225 rpm, 29° C., for 48 hours. 2.5 mL were inoculated into 25 mL ERY-P medium (5% dextrose, 3% Nutrisoy flour, 0.3% $(NH_4)_2SO_4$, 0.5% NaCl, 0.6% $CaCO_3$. pH adjusted to 7.0) and incubated at 225 rpm, 29° C., for a total of 6 days. Butyric acid was added to the flask at 24, 72 and 120 hours (400 ppm, 400 ppm, 200 ppm, respectively). Whole broth pH was then adjusted to 9.1 using 1N NaOH. The sample was extracted twice with an equal volume of ethyl acetate. Ethyl acetate phases were concentrated to dryness under nitrogen (50° C. water bath), then resuspended in 1.0 mL methanol for HPLC-MS analysis. This confirmed the production of 6-deoxy-13-propyl-erythromycin B.

HPLC retention time—Method C—23.5 minutes

APCI-MS-(M+H)$^+$ observed at m/e 716, required for $C_{38}H_{70}NO_{11}$–716

EXAMPLE 18

Evaluation of Antibacterial Activity

An in vitro antibacterial assay was performed in microtiter and interpreted according to *Performance Standards for Antimicrobial Disk Susceptibility Tests—Sixth Edition: Approved Standard*, published by The National Committee for Clinical Laboratory Standards (NCCLS) guidelines. Minimum inhibitory concentrations(MICs) were obtained versus various bacteria. For example, *Staphylococcus aureus* 80CR5 (macrolide susceptible strain) afforded values generally ranging from ≦0.1 to 1.56 μg/m L.

What is claimed is:

1. A process for preparing a compound of formula 1:

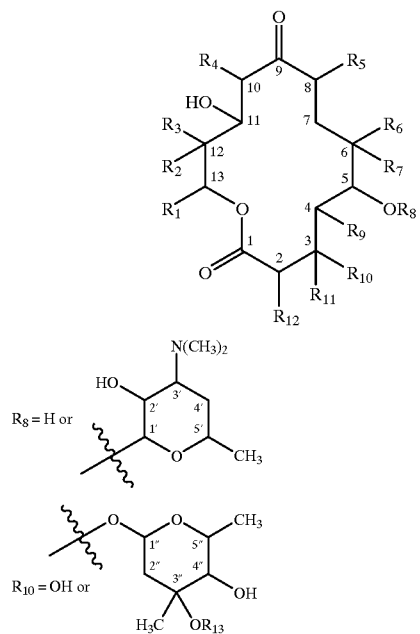

and to pharmaceutically acceptable salts thereof, wherein:

$R_1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R_1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R_1$ may be with formula (a) as shown below:

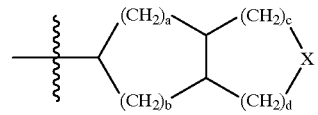

wherein X is O, S or —$CH_2$—, a, b, c, and d are each independently 0–2 and a+b+c+d≦5;

$R_2$ is H or OH; $R_3$–$R_5$ are each independently H, $CH_3$, or $CH_2CH_3$; $R_6$ is H or OH; and $R_7$ is H, $CH_3$, or $CH_3CH_2$; $R_8$ is H or desosamine; $R_9$ is H, $CH_3$, or $CH_2CH_3$; $R_{10}$ is OH, mycarose ($R_{13}$ is H), or cladinose ($R_{13}$ is $CH_3$), $R_{11}$ is H; or $R_{10}$=$R_{11}$=O; and $R_{12}$ is H, $CH_3$, or $CH_2CH_3$; or any of the above defined compounds modified by replacing one or more —CHOH or —CHOR groups by a keto group, which comprises fermenting an organism capable of producing erythromycin in the presence of a carboxylic acid of the formula $R_1CO_2H$ wherein $R_1$ is as defined hereinabove, or a salt, ester or amide thereof or oxidative precursor thereof, and isolating the compound of formula 1.

2. A process of claim 1, wherein the organism is *Saccharopolyspora erythraea* and which may optionally contain an effectively integrated plasmid capable of directing the biosynthesis of compounds of formula 1; said plasmid may optionally contain a Type II PKS promoter/activator gene.

3. A process of claim 2, wherein the organism *Saccharopolyspora erythraea* is selected from strains NRRL 2338, 18643 or 21484 which may optionally contain an effectively integrated plasmid capable of directing the biosynthesis of compounds of formula 1; said plasmid may optionally contain the $act^I$ promoter and its cognate activator gene $act^{II}$-$orf^4$.

4. A process of claim 3, wherein the optionally effectively integrated plasmids is pAVLD, pIG1, pND30, pCJR26, pCJR49, pC-AT12, pc-ATX or other similar constructs.

5. A process of claim 3, wherein the organism is *S. erythraea* ERMD1, *S. erythraea* NRRL 2338/pIG1, *S. erythraea* NRRL 2338/pND30, or other similar tranformants.

6. A process for preparing a compound of formula 2:

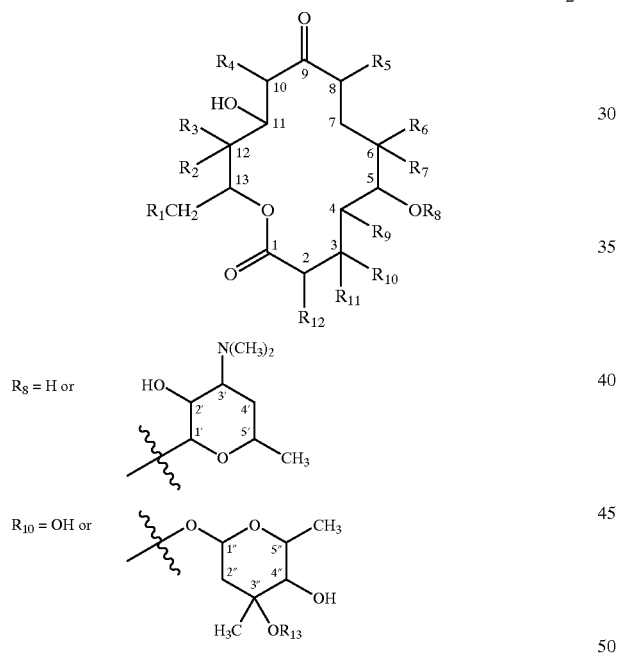

and to pharmaceutically acceptable salts thereof, wherein:

$R_1$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$–$C_8$ cycloalkyl or $C_5$–$C_8$ cycloalkenyl either of which may be optionally substituted by methyl or one or more $C_{1-4}$ alkyl groups or halo atoms; or a 3 to 6 membered oxygen or sulphur containing heterocyclic ring which may be saturated or fully or partially unsaturated and which may optionally be substituted by one or more $C_1$–$C_4$ alkyl groups or halo atoms; or a group of the formula $SR_{14}$ wherein $R_{14}$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3–6 membered oxygen or sulphur-containing heterocyclic ring which may be saturated, or fully or partially unsaturated and which may optionally be substituted by one or more $C_1$–$C_4$ alkyl groups or halo atoms;

$R_2$ is H or OH; $R_3$–$R_5$ are each independently H, $CH_3$, or $CH_2CH_3$; $R_6$ is H or OH; and $R_7$ is H, $CH_3$, or $CH_3CH_2$; $R_8$ is H or desosamine; $R_9$ is H, $CH_3$, or $CH_2CH_3$; $R_{10}$ is OH, mycarose ($R_{13}$ is H), or cladinose ($R_{13}$ is $CH_3$), $R_{11}$ is H; or $R_{10}$=$R_{11}$=O; and $R_{12}$ is H, $CH_3$, or $CH_2CH_3$, with the proviso that when $R_3$–$R_5$ are $CH_3$, $R_7$ is $CH_3$, $R_9$ is $CH_3$ and $R_{12}$ is $CH_3$, then $R_1$ is not H or $C_1$ alkyl; or any of the above defined compounds modified by replacing one or more —CHOH or —CHOR groups by a keto group, which comprises fermenting an organism capable of producing erythromycin in the presence of a carboxylic acid of the formula $R_1CO_2H$ wherein $R_1$ is as defined hereinabove, or a salt, ester or amide thereof or oxidative precursor thereof, and isolating the compound of formula 2.

7. A process of claim 6, wherein the organism is *Saccharopolyspora erythraea* and which may optionally contain an effectively integrated plasmid capable of directing the biosynthesis of compounds of formula 2; said plasmid may optionally contain a Type II PKS promoter/activator gene.

8. A process of claim 7 wherein the organism *Saccharopolyspora erythraea* is selected from strains NRRL 2338, 18643 or 21484 which may optionally contain an effectively integrated plasmid capable of directing the biosynthesis of compounds of formula 2 said plasmid may optionally contain the $act^I$ promoter and its cognate activator gene $act^{II}$-$orf^4$.

9. A process of claim 8 wherein the optionally effectively integrated plasmids is pAVLD, pIG1, pND30, pCJR26, pCJR49, pC-AT12, pc-ATX or other similar constructs.

10. A process of claim 8 wherein the organism is *S. erythraea* ERMD1, *S. erythraea* NRRL 2338/pIG1, *S. erythraea* NRRL 2338/pND30, or other similar tranformants.

* * * * *